(12) United States Patent
Rabinovitz et al.

(10) Patent No.: US 11,947,786 B2
(45) Date of Patent: Apr. 2, 2024

(54) SYSTEM AND METHOD FOR CONTROLLING THE DISPLAY OF AN IMAGE STREAM

(71) Applicant: Given Imaging LTD., Yoqneam (IL)

(72) Inventors: Raphael Rabinovitz, Hod Hasharon (IL); Ady Ecker, Nes-Ziona (IL); Hagai Krupnik, Nofit (IL); Boaz Ben Nahum, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 0 days.

(21) Appl. No.: 17/899,675

(22) Filed: Aug. 31, 2022

(65) Prior Publication Data
US 2022/0413692 A1  Dec. 29, 2022

Related U.S. Application Data

(63) Continuation of application No. 15/103,489, filed as application No. PCT/IL2014/051087 on Dec. 11, 2014, now Pat. No. 11,609,689.
(Continued)

(51) Int. Cl.
*G06F 3/04847* (2022.01)
*A61B 1/04* (2006.01)
(Continued)

(52) U.S. Cl.
CPC .......... *G06F 3/04847* (2013.01); *A61B 1/041* (2013.01); *G06F 3/03543* (2013.01);
(Continued)

(58) Field of Classification Search
CPC . G06F 3/04847; G06F 16/743; G11B 27/005; A61B 1/041; G06T 7/0012; H04N 5/783
See application file for complete search history.

(56) References Cited

U.S. PATENT DOCUMENTS

| | | | |
|---|---|---|---|
| 5,586,216 A | 12/1996 | Degen et al. | |
| 5,920,317 A | 7/1999 | McDonald | |

(Continued)

FOREIGN PATENT DOCUMENTS

| | | |
|---|---|---|
| CN | 102859552 A | 1/2013 |
| WO | 2007136138 A1 | 11/2007 |
| WO | 2009035212 A1 | 3/2009 |

*Primary Examiner* — Nicholas Ulrich
(74) *Attorney, Agent, or Firm* — Carter, DeLuca & Farrell LLP

(57) ABSTRACT

Embodiments of the invention are related to a system and method of controlling a display of an image stream. The system may include a memory to store the image stream; the image stream may comprise a plurality of image frames. The system may further include a processor configured to execute the method. The moving image stream may be displayed to a user in an image stream display area of a screen and a frame rate control interface may be generated on a speed control area of the screen, such that the image stream display area is horizontally adjacent to the speed control area. An indication of a desired frame rate for displaying the image stream of the image frames may be received from the user, in that the frame rate may be selected according to a location of a pointing indicator in the speed control area.

18 Claims, 13 Drawing Sheets

Related U.S. Application Data

(60) Provisional application No. 61/914,494, filed on Dec. 11, 2013.

(51) Int. Cl.

| | | |
|---|---|---|
| *G06F 3/0354* | (2013.01) | |
| *G06F 3/0362* | (2013.01) | |
| *G06F 16/74* | (2019.01) | |
| *G06F 16/955* | (2019.01) | |
| *G06T 7/00* | (2017.01) | |
| *G11B 27/00* | (2006.01) | |
| *G11B 27/10* | (2006.01) | |
| *G11B 27/34* | (2006.01) | |
| *G06F 3/0485* | (2022.01) | |
| *G16H 40/63* | (2018.01) | |

(52) U.S. Cl.
CPC .......... *G06F 3/0362* (2013.01); *G06F 16/743* (2019.01); *G06F 16/9562* (2019.01); *G06T 7/0012* (2013.01); *G11B 27/005* (2013.01); *G11B 27/102* (2013.01); *G11B 27/34* (2013.01); *G06F 3/0485* (2013.01); *G06T 2207/30028* (2013.01); *G16H 40/63* (2018.01)

(56) References Cited

U.S. PATENT DOCUMENTS

| | | |
|---|---|---|
| 6,173,317 B1 | 1/2001 | Chaddha et al. |
| 6,709,387 B1 | 3/2004 | Glukhovsky et al. |
| 7,505,062 B2 | 3/2009 | Davidson et al. |
| 7,684,599 B2 | 3/2010 | Horn et al. |
| 8,045,012 B2 | 10/2011 | Miyanohara |
| 8,128,476 B1 | 3/2012 | Sidhu et al. |
| 8,423,123 B2 | 4/2013 | Horn |
| 2002/0093484 A1 | 7/2002 | Skala et al. |
| 2002/0130976 A1 | 9/2002 | Gutta et al. |
| 2002/0177779 A1 | 11/2002 | Adler et al. |
| 2003/0151661 A1 | 8/2003 | Davidson et al. |
| 2003/0208107 A1 | 11/2003 | Refael |
| 2005/0075537 A1 | 4/2005 | Chen et al. |
| 2007/0060798 A1 | 3/2007 | Krupnik et al. |
| 2007/0103739 A1* | 5/2007 | Anderson, Jr. ...... G03B 21/118 358/487 |
| 2007/0211928 A1 | 9/2007 | Weng et al. |
| 2008/0051642 A1 | 2/2008 | Krupnik |
| 2008/0198268 A1 | 8/2008 | Tullberg |
| 2008/0270395 A1 | 10/2008 | Gossweiler, III et al. |
| 2008/0317386 A1 | 12/2008 | Wood et al. |
| 2009/0284589 A1 | 11/2009 | Radeva et al. |
| 2012/0054670 A1 | 3/2012 | Rainisto |
| 2012/0113239 A1* | 5/2012 | Krupnik ............... A61B 1/0005 348/E7.085 |
| 2013/0002842 A1 | 1/2013 | Das et al. |
| 2013/0002968 A1 | 1/2013 | Bridge et al. |
| 2013/0021372 A1 | 1/2013 | Wiemker et al. |
| 2013/0031589 A1* | 1/2013 | Casanova ...... H04N 21/234381 725/91 |
| 2013/0132374 A1 | 5/2013 | Olstad et al. |
| 2013/0138717 A1 | 5/2013 | Lingley |
| 2013/0311885 A1 | 11/2013 | Wang et al. |
| 2014/0059432 A1 | 2/2014 | Johansson et al. |
| 2014/0108929 A1 | 4/2014 | Garmark et al. |
| 2014/0303435 A1 | 10/2014 | Taniguchi |
| 2017/0068361 A1 | 3/2017 | Imbruce et al. |

* cited by examiner

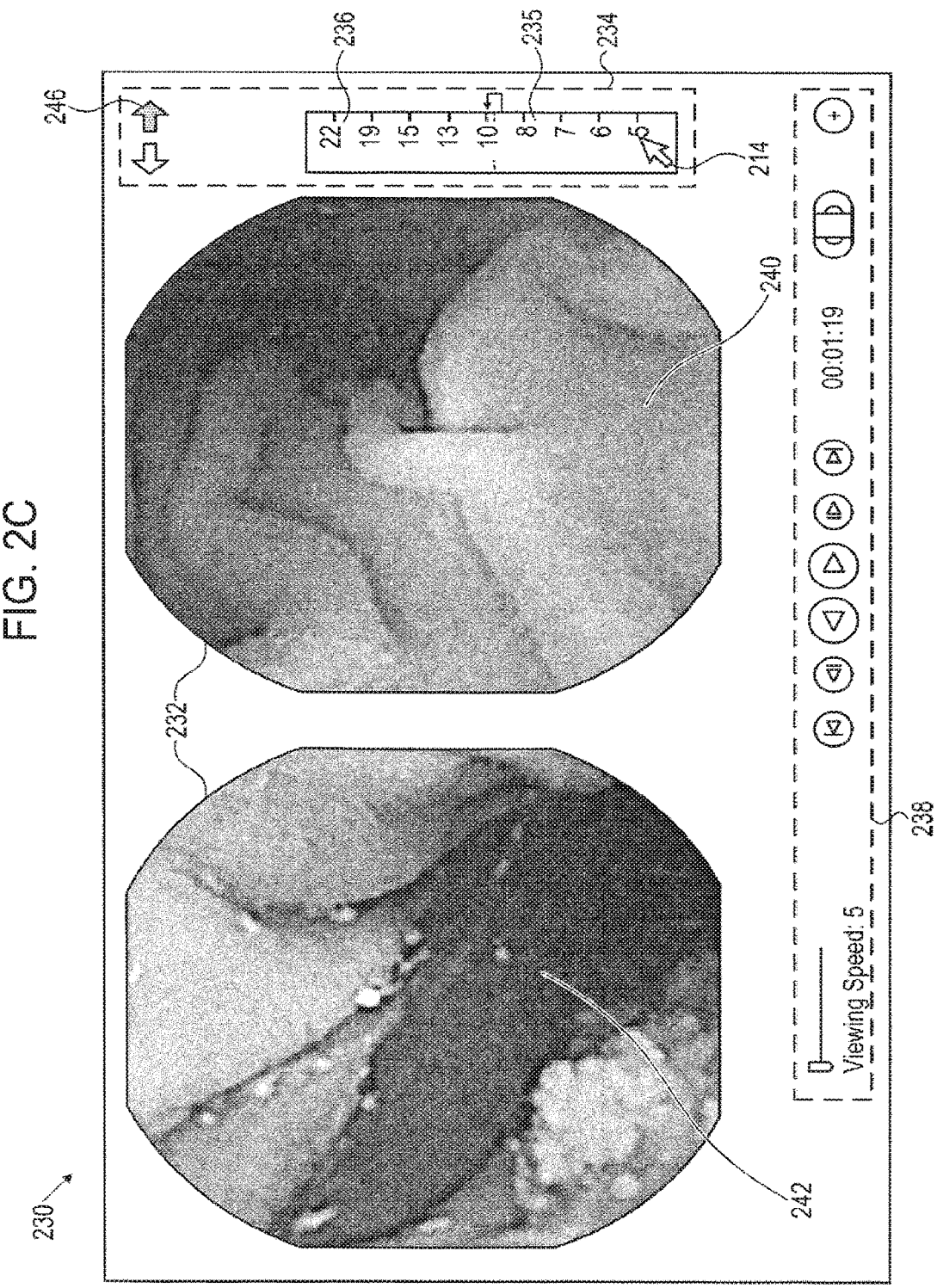

SYSTEM AND METHOD FOR CONTROLLING THE DISPLAY OF AN IMAGE STREAM

CROSS-REFERENCE TO RELATED APPLICATIONS

This application is a Continuation of U.S. patent application Ser. No. 15/103,489, filed Jun. 10, 2016, which is a U.S. National Stage Application of International Application No. PCT/IL2014/051087, filed Dec. 11, 2014, which in turn claims priority to, and the benefit of the filing date of, U.S. Provisional Application No. 61/914,494, filed Dec. 11, 2013. The entire contents of each of the foregoing applications are hereby incorporated by reference herein.

FIELD OF THE INVENTION

The present invention is generally related to controlling a display of moving image frames and more specifically to providing to a user tools for controlling the display.

BACKGROUND OF THE INVENTION

Inspecting movies or moving image streams frame by frame for detecting abnormal behavior is an activity performed daily by many different users having different professions. Examples include, security professionals, watching movies from surveillance cameras looking for unusual behavior, or doctors watching movies or streams of images from within the human body taken by an imaging device such as swallowable capsules including a camera. The amount of graphical data to be inspected may be enormous. Such inspection activity may impose heavy burden on the user's senses and alertness.

Often, the majority of the movie frames do not contain any abnormal behavior or any interesting or suspicious finding. These frames are preferably inspected at relatively higher speed (e.g., measured in frames per second), to shorten the inspection time and not tire the user inspecting the movie. When a suspicious finding is detected the user may need to inspect it more carefully, at for example, a lower frame rate, and go backwards in the movie to review certain frames again if necessary. Furthermore, the image stream may have segments which are substantially static, and segments which include relatively high activity or a large number of interesting frames.

Most movie inspecting applications have a control application including a speed control. If such a control application is to be displayed on the screen it may include a speed control key (e.g., a speed bar) below (or at the lower part) of the display area of the movie's frames. The control applications may include key(s) to stop/start the movie (stream of images) and change the direction of stream backward/forward. When using the various control keys of such control applications, the user is required to take his eyes off the inspected frame, direct his vision down to the control keys, and then click a pointing device, such as mouse or touch a touch-screen in order to change the mode in which the movie is being played. For example, in order to change the speed of the moving frames, the user must point the speed bar and then click and drag a speed marker to the desired speed. When inspecting a movie at for example, a speed of 20 frames per second, missing the stream of even one second may result in losing 20 frames that may include suspicious behavior or frames of potential interest (e.g., a criminal activity or a pathology candidate).

Furthermore, in case the user does not use a control application in order to change the speed or the direction of the image stream, for example, in order not to miss important frames, and continues to watch the image stream at a constant rate passively (e.g., with minimum interaction with the image stream) the user may get tired and lose his or her concentration. A speed control application that may allow and encourage the user to actively interact with the image stream without moving his vision from the images, for example, by changing the speed and/or direction of the image stream displayed, may allow the user to stay more focused and alert, thus may reduce the chance of the user missing an important finding. Allowing the user to view the stream at a higher frame rate in sections of less interest may shorten the time of the inspection and increase the user alertness.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 2A-2C show examples of screens according to some embodiments of the present invention;

Figure 1A:
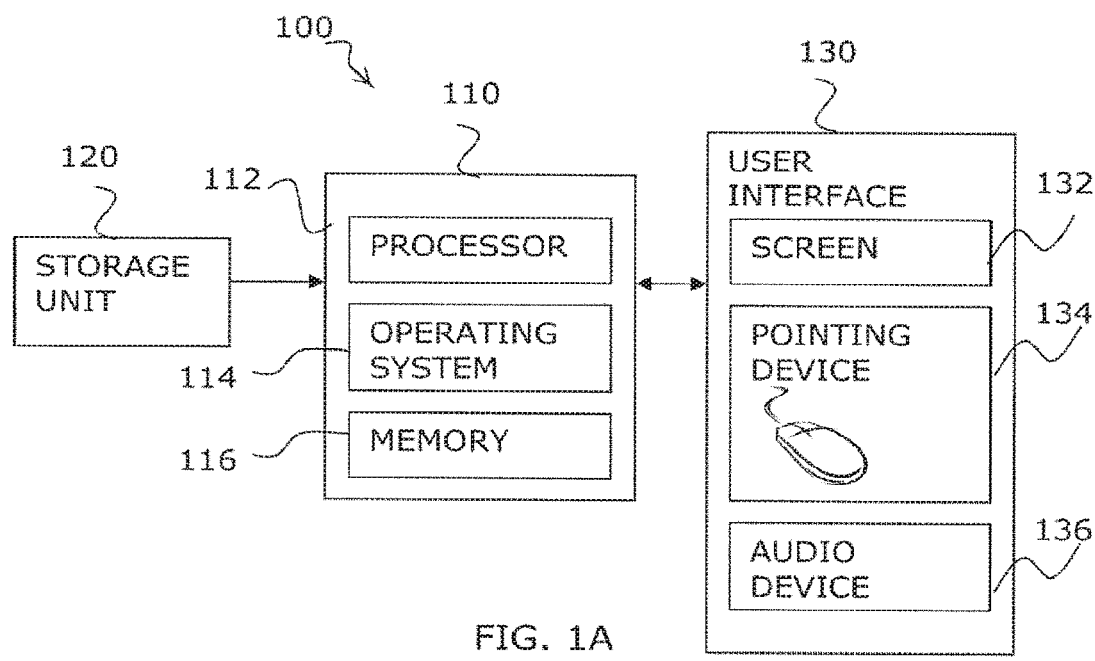
FIG. 1A shows a high level block diagram of an example of a computing device according to some embodiments of the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", "selecting", "associating", "generating", "displaying" or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently.

Embodiments of the present invention may be related to a system and a method for controlling a display of an image stream to be inspected by a user. Some examples may include, image frames captured in the colon by an imaging capsule including an imager, or image frames captured by a surveillance camera. A user (e.g., a doctor or a security professional) may need to inspect the stream of image frames for detecting one or more frame sequences of interest or potential interest (e.g., to a user or medical professional) including, for example, possibly suspicious behavior or a possibly interesting pathology candidate. The ability of the user to properly inspect all the image frames may be dependent on the alertness of the user. Allowing the user to easily control the frame rate (e.g., speed of the moving frames), to change the stream playback direction (backward or forward) and/or to stop and start the stream playback without moving his/hers eyes from the image frames, may result in a decreased risk of losing information shown in the stream images.

To assist in maintaining a more alert user, a system according to some embodiments of the invention may include a control interface (e.g., a control application) that may encourage the user to actively change viewing parameters controlling the display of the moving frames (e.g., frame rate, start/stop, playback direction, etc.). The control interface may be located adjacent to the moving frames. The control interface may be significantly large (in comparison to commonly known control interfaces) to allow a user to direct his vision at the moving image frames and at the control interface at the same time. Furthermore, the system may generate alerts to the user during the inspection of the moving image frames. The alerts may be given to the user as graphical marking and/or as a sound (thus providing a predetermined indication), a predefined time (e.g., 2 seconds) or a predefined number of frames before a frame sequence of interest (included in the moving image frames) is to be displayed or is reached. The frame sequence of interest may be determined using a program or an application for automatic detection of abnormal behavior or suspicious findings.

As used herein, a user may be a person that inspects an image stream including a plurality of image frames (e.g., a movie) captured by a camera or an imager, in order to find abnormal behavior, pathology candidates or any other findings determined by the user. The user may be a doctor or a medical professional, a security professional, a scientist, a researcher or the like.

As used herein, a frame sequence of interest may include any number, at least two, of consecutive frames that were indicated by the user as "interesting" or which may be potentially interesting to a user, and thus may require inspection at a lower speed. The frame sequence of interest may include, for example, image(s) of a potential pathology, unusual behavior, any frames that the user may want to inspect, or an embodiment of the invention determines that the user may want to inspect, more closely or at a lower speed. Additionally or alternatively, the frame sequence of interest may include frames that were taken when the imaging device (e.g., an imaging capsule) moved at a higher speed, or when an object captured by the imaging device (e.g., a suspect captured by a surveillance camera) moved at a higher speed.

Reference is made to FIG. 1A, showing a high level block diagram of an example of a system for controlling the display of moving stream of image frames according to some embodiments of the present invention. A system 100 may include a computer processing device 110, a storage unit 120 and a user interface 130. Processing unit 110 may include a processor 112 that may be, for example, a central processing unit (CPU), a chip or any suitable computing or computational device, an operating system 114 and a memory 116. System 100 may be included in a desktop computer, laptop commuter, a tablet, a mainframe computer or the like. Processor 112 or other processors such as processor 17 or processor 13 (in FIG. 1B) may be configured to carry out methods according to embodiments of the present invention by for example executing instructions stored in a memory such as memory 116.

Operating system 114 may be or may include any code segment designed and/or configured to perform tasks involving coordination, scheduling, arbitration, supervising, controlling or otherwise managing operation of processing device 110, for example, scheduling execution of programs.

Operating system 114 may be a commercial operating system. Memory 116 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 116 may be or may include a plurality of, possibly different memory units.

Memory 116 may store any executable code, e.g., an application, a program, a process, task or script. The executable code may include codes for controlling the display of an image stream or any other codes or instruction for executing methods according to embodiments of the present invention. The executable code may be executed by processor 112 possibly under control of operating system 114.

Storage 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data manipulated according to embodiments disclosed herein, such as images, image frames, or an image stream, may be stored in for example storage 120 and/or memory 116. Content may be stored in storage 120 and may be loaded from storage 120 into memory 116 where it may be processed by processor 112. For example, storage 120 may include an image stream including a plurality of image frames, data related to the image frames and/or data related to abnormal findings or suspicious behavior according to embodiments of the invention.

User interface 130 may be or may include a screen 132 (e.g., a monitor, a display, a CRT, etc.), a pointing device 134 and an audio device 136. User interface 130 may include or be associated with other input devices such as, a keyboard. Pointing device 134 may be a mouse, a touch screen or a pad or any other suitable device that allows a user to control (e.g., by hand or finger movements) a pointing indicator (e.g., a cursor) located on screen 132. Screen 132 may be any screen suitable for displaying image steam and a controlling interface. In some embodiments, screen 132 and pointing device 134 may be included in a single device, for example, a touch screen. It will be recognized that any suitable number of pointing devices may be included in user interface 130. User interface 130 may include audio device 136 such as one or more speakers, earphones and/or any other suitable audio devices. It will be recognized that any suitable number of output devices may be included in user interface 130. Any applicable input/output (I/O) devices may be connected to processing unit 110. For example, a wired or wireless network interface card (NIC), a modem, printer or facsimile machine, a universal serial bus (USB) device or external hard drive may be included in user interface 130.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

The storage medium may include, but is not limited to, any type of disk including floppy disks, optical disks, compact disk read-only memories (CD-ROMs), rewritable compact disk (CD-RWs), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage unit.

A system according to embodiments of the invention may include components such as, but not limited to, a plurality of central processing units (CPU) or any other suitable multipurpose or specific processors or controllers, a plurality of input units, a plurality of output units, a plurality of memory units, and a plurality of storage units. A system may additionally include other suitable hardware components and/or software components. In some embodiments, a system may include or may be, for example, a personal computer, a desktop computer, a mobile computer, a laptop computer, a notebook computer, a terminal, a workstation, a server computer, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Figure 1B:
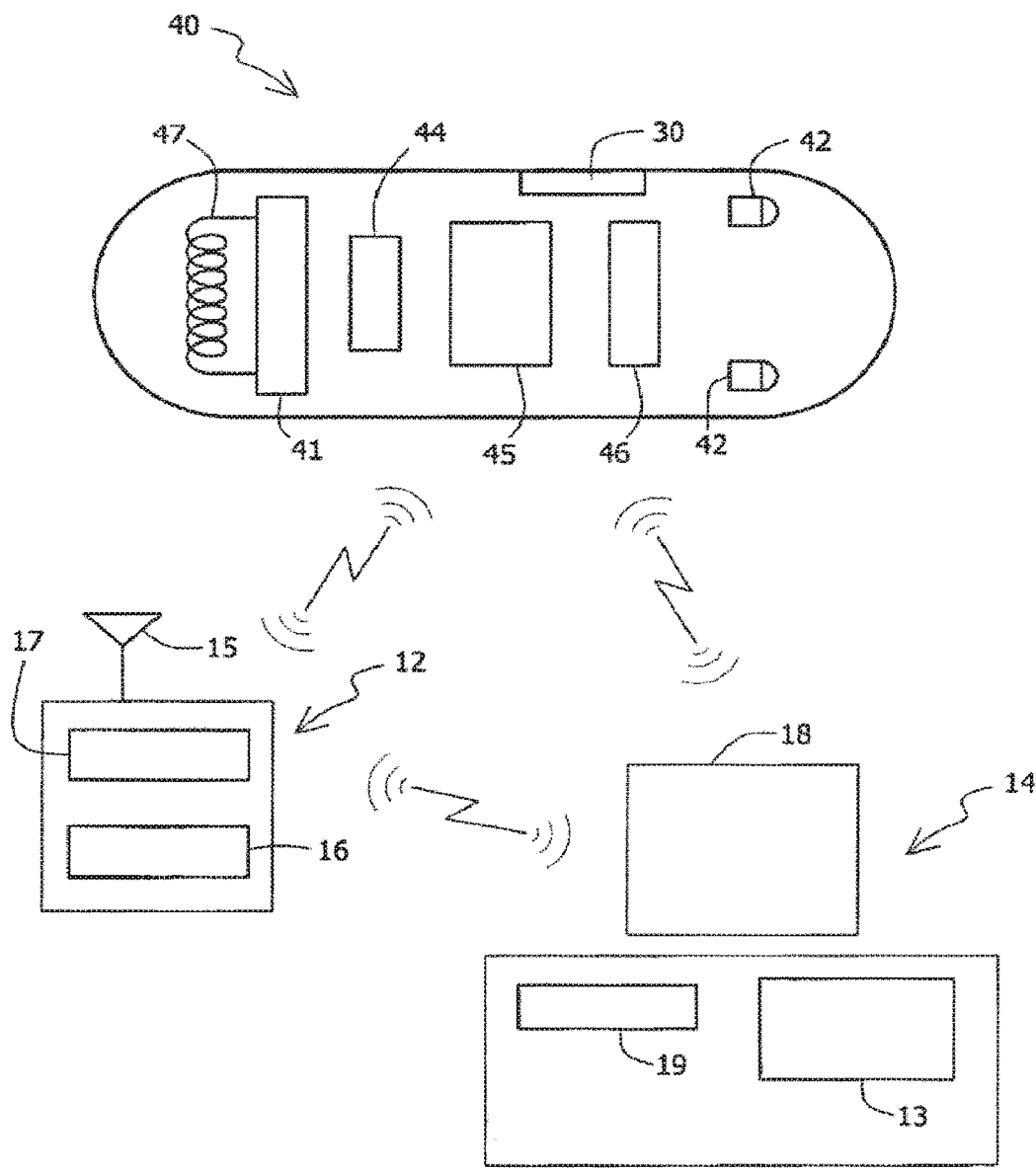
FIG. 1B shows a high level block diagram of an example of an imaging system according to some embodiments of the invention.

Reference is made to FIG. 1B, which shows a schematic diagram of an imaging system having, for example, an in-vivo imaging system according to an embodiment of the present invention. The imaging system may include an imaging device (e.g., a capsule) such as an in-vivo imaging device 40, an external receiving device and/or recording device 12, e.g. data receiver, and a workstation 14. The imaging device 40 may have an imager 46, for capturing image frames or a stream of image frames, an illumination source 42, for illuminating the body lumen, a power source 45 for powering device 40 and a processor 44 for processing data and commands to and from imaging device 40. In vivo-imaging device 40 may also include a transmitter 41 with antenna 47, for transmitting image and possibly other data to an external receiver 12. In some embodiments of the present invention, imaging device 40 may include one or more sensors 30, in addition to imager 46, for example, temperature sensors, pH sensors, pressure sensors, blood sensors, tracking sensors, etc. Imager 46 may be a CCD or CMOS imager, or may be another solid state imaging device or other imaging device. Illumination source 42 may include one or more LEDs or other illumination sources. In some embodiments of the present invention, imaging device 40 may be an autonomous device, a capsule, or a swallowable capsule. In other embodiments of the present invention, device 40 may not be autonomous, for example, device 40 may be an endoscope or other in-vivo imaging device The imaging device 40 may transmit information (e.g., images or other data) to an external receiver 12 possibly close to or worn on a subject. Receiver 12 may include an antenna or antenna array 15 and a data receiver storage unit 16. Antenna array 15 may pick up signals transmitted by device 40 or the transmitter 41 and antenna 47 of device 40. The external receiver 12 may include one or more processors 17 for processing image data or other data. Receiver 12 (and/or device 40) may include a localization unit (not illustrated), for determining the location of an autonomous in-vivo imaging device 40 over time. For example, the localization unit may track the location or position of device 40 in three-dimensional space over time and/or may track the distance, for example the distance over time that device 40 traveled through the gastrointestinal (GI) tract or through a specific organ in the GI tract over time.

The receiver 12 may take on other suitable configurations and may not include an antenna or antenna array. In one embodiment of the present invention, the receiver 12 may, for example, include an LCD display for displaying image data or other data, e.g. location data. In other embodiments, receiver 12 may be electrically connected, e.g., via wire, the Bluetooth system, or wireless connection, to a display unit, e.g., display unit 18 or workstation 14, to display data transmitted by in-vivo device 40 and/or processed by processing unit 17, 44, or workstation 14.

In one embodiment of the present invention, the receiver 12 may, for example, receive and store data from imaging device 40, e.g. an image stream data captured and/or processed by processor 17. The data may be stored in storage unit such as storage unit 120 included in system 100. The stored data may later be transferred to a workstation 14, such as a personal computer, laptop or other portable or stationary computing devices, where the data may be further analyzed, stored, and/or displayed to a user, e.g. a health professional. Workstation 14 may include some or all of the components of system 100. System 100 may be included in workstation 14. Typically, workstation 14 may include processor 13 (e.g., unit 110 and processor 112), data processor storage unit 19 (e.g., storage unit 120), a disk drive (e.g., memory 116), input-output devices (e.g., user interface 130), and display unit 18 (e.g., screen 132). Display unit 18 may include a monitor, although alternate configurations are possible. Processing unit 13 may typically, as part of its functionality, act as a controller controlling the display of data for example, image data or other data. In one example, processor 13 and/or processor 17 may be employed to control the display of an image stream. In one embodiment, processor 13 and/or processor 17 may be employed to generate an alert to a user during screening of the image stream.

Display unit 18 may typically be a conventional video display, but may, in addition, be any other device capable of providing image or other data. Instructions or software for carrying out a method according to an embodiment of the invention may be included as part of workstation 14, for example stored in memory 19.

Figure 2A:
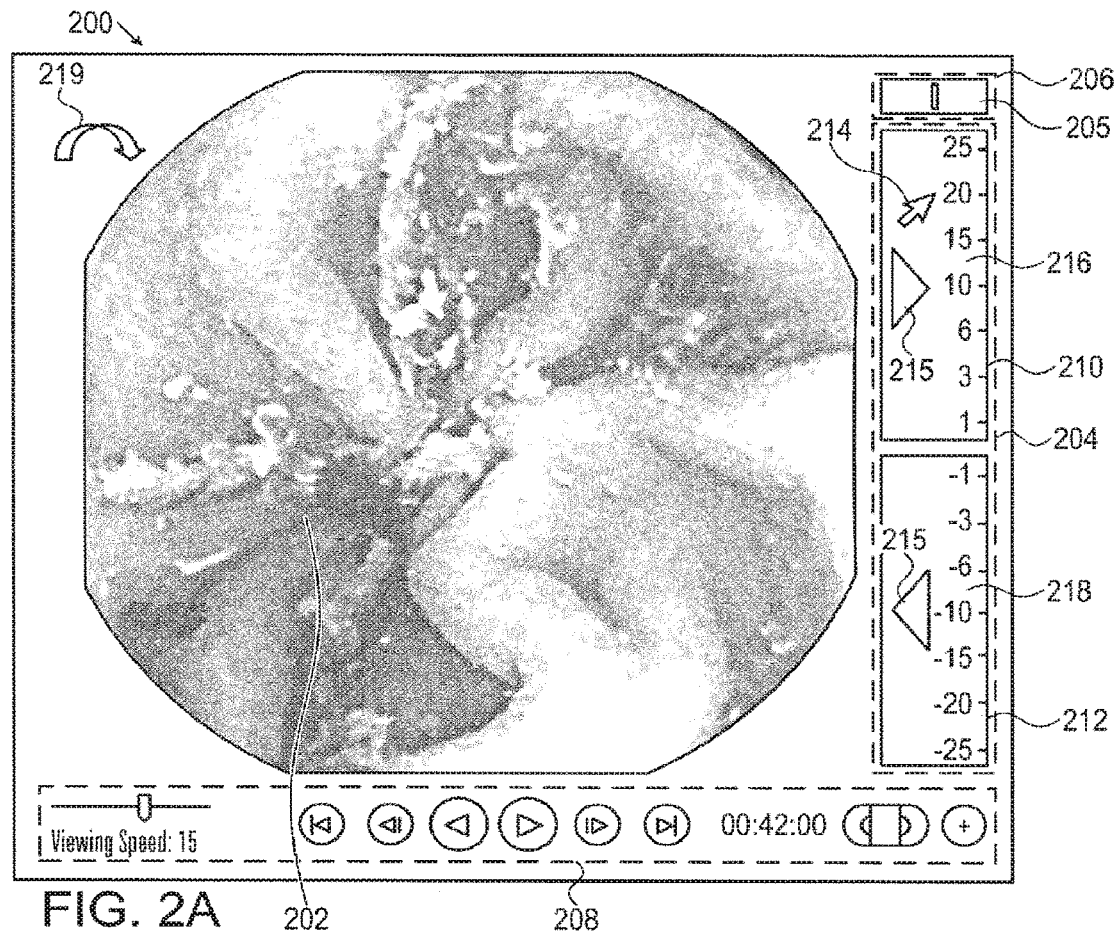
Figure 2B:
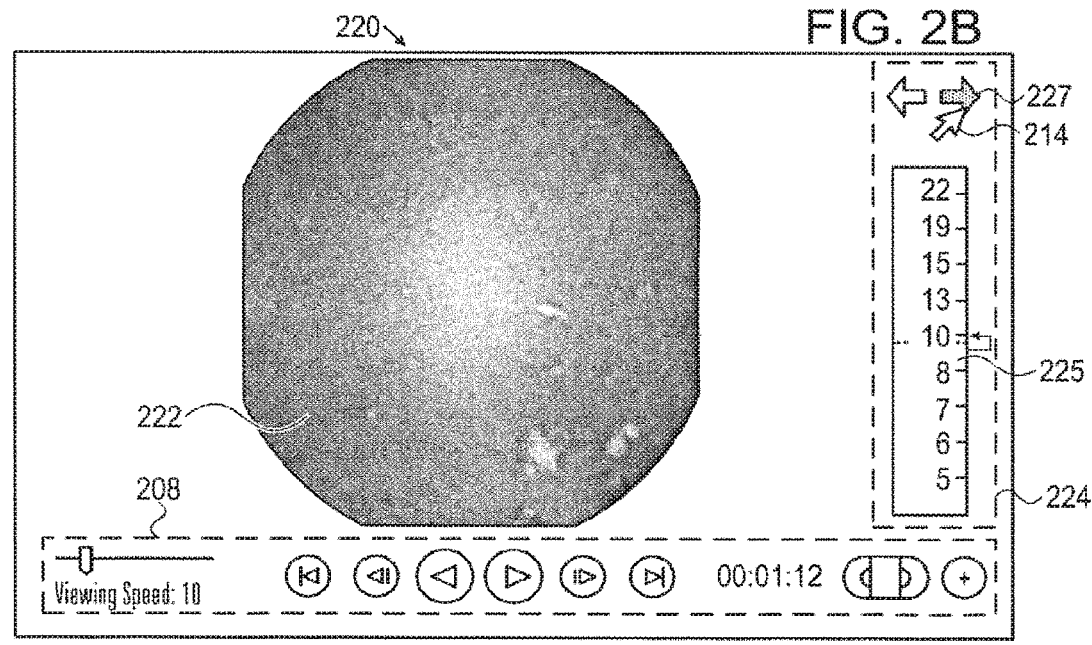

Reference is made to FIGS. 2A-2C, showing examples of interface screens or displays provided to the user for example via screen or monitor 132 according to some embodiments of the invention. FIG. 2A shows an example of interface display 200 having at least an image stream display area 202 and a speed control area 204. In some embodiments, screen 200 may further include a stream advancement portion 206 and a horizontal control area 208. Image stream display area 202 may include a display including an image stream. A processor (e.g., processor 112) may display to a user (or cause screen or monitor to display) the display including the image stream in image stream display area 202. Other processors, such as processor 17 or processor 13, may carry out all or part of the embodiments of the invention. For example, the processor may display image frames captured by an imaging device included in an imaging capsule from at least one organ in the gastrointestinal tract, as illustrated in FIG. 2A. In yet another example, the processor may display image frames captured by a surveillance camera in a bank.

Speed control area 204 may include a frame rate control scales 216 and/or 218 for controlling the frame rate in which the image frames are to be displayed in the image stream display area. A desired frame rate for displaying the stream of the image frames may be selected according to a location of a pointing indicator 214 (e.g., a cursor or a graphic mark such as an arrow or a small hand that may be controlled by pointing device 134 (e.g., a mouse)) on frame rate scale 216 and/or 218 in speed control area 204. A pointing indicator as used herein may be defined as a movable symbol or any of various means of identifying or pointing to a particular position on a computer screen. The user may change the frame rate (e.g., the number of image frames per second displayed by a processor) by moving pointing indicator 214 inside speed control area 204 using a pointing device (e.g., pointing device 134) by, for example, moving pointing indicator 214 vertically, e.g. upwards or downwards over the area of frame rate scale 216 and/or 218, to select a value indicating the desired frame rate (e.g., 20 frames/second as illustrated). The vertical motion may be a more natural movement for the human arm or hand than horizontal movement, and may be easier for the user to operate without focusing his/her vision at the control interface in speed control area 204. In one embodiment a movement of the pointing indicator inside the speed control area (e.g., the user using a pointing device to move the pointing indicator) may indicate a desired change in the frame rate, and may cause the system to alter the frame rate.

Additionally or alternatively, speed control area 204 may include a forward/backward direction control interface to set the playback direction of the image frames. For example, as illustrated in FIG. 2A, the speed control area may be divided into two sub-portions 210 and 212. Moving pointing device 134 such that pointing indicator 214 is placed in sub-portion 210 may cause the stream of images to be played in the forward direction and placing pointing indicator 214 in the sub-portion 212 may cause the stream of images to be played in the backwards direction. The "forward" direction, when referred to herein, indicates that the movie is played back in the chronological order of capturing the image frames by the imaging device, e.g., starting from the frames that was captured earliest, and playing the frames which were captured sequentially after it in time. The "backward" or reverse direction, when referred to herein, indicates that the movie is played back sequentially, in the opposite order of the chronological capturing order of the frames, e.g., starting from a certain frame which the user selected, the frames are played back sequentially according to the descending time or order of capture. In some embodiments, the selection of the forward/backwards direction may include placing (e.g., by moving pointing device 134) pointing indicator 214 at one or more graphic marks 215 such as the large triangles 215 shown in sub-portions 210 and 212, as illustrated in FIG. 2A. One or more graphic marks 227 may be included in a single portion as shown in the upper end of speed control area 224 in FIG. 2B.

Screen 200 may further include a change direction alerting mark 219. Mark 219 may appear on screen 200 (or screens 220 or 230) each time the playing or streaming direction of the images changes, either by intentional or unintentional movement of pointing device 134 such that pointing indicator 214 may be placed or moved over marks 215 or 227. Change direction alerting mark 219 may appear at any portion of area of screens 200, 220 or 230 such that a user observing mark 219 may keep his/her vision focus on the images displayed, for example, in the upper left portion of screen 200, as illustrated in FIG. 2A. In the embodiment shown in FIG. 2A sub-portion 210 may include a frame rate scale 216 for selecting the frame rate for the forward direction and portion 212 may include a frame rate scale 218 for selecting the frame rate for the backward direction (backward being opposite to the order in which the frames were collected).

Image stream display area 202 and speed control area 204 may be located on screen 200 such that a user may direct his vision or gaze to image stream display area 202 of the screen while moving the pointing indicator 214 (by moving pointing device 134) in speed control area 204. The user may view the speed control area 204 by using only his/her peripheral vision, allowing the user to obtain some visual information from speed control area 204, while concentrating or focusing his vision (the details obtained by focusing images on the fovea) on image stream display 202. The location of image stream display area 202 in relation to speed control area 204 may be such that the user may easily direct his vision to both areas, or obtain useful information from both areas, substantially without moving his eyes from image stream display area 202. Thus, controlling the display of the stream of images may be performed by a user while maintaining a focused vision on the images displayed. In some embodiments, image stream display area 202 may be horizontally adjacent (when the screen is displayed as intended on a monitor) to speed control area 204, as illustrated in FIG. 2A. In some embodiments, speed control area 204 may be larger than a threshold value; the threshold value may be calculated based on the area of the image stream display area. For example, the area of speed control area 204 may be, for example, in the range of approximately 1/10 to 1/3 of the area of the image stream display area 202.

In the embodiment shown in FIG. 2A screen 200 may include an orientation area (or sub-portion 206) such that speed control area 204 is for selecting a forward direction for displaying the stream of the image frames and the stream advancement portion 206 is for selecting a backward (e.g., backward in time or frame sequence) direction for displaying the stream of the image frames. Moving from forward to backward directions is performed by moving the pointing indicator 214 from the speed control area 204 to orientation area 206 of screen 200.

In some embodiments, selecting the location of the pointing indicator (e.g., indicator 214) may be performed without clicking on the pointing device (e.g., pointing device 134) or providing another indication. The user may select a frame rate simply by placing (e.g., hovering, without clicking) the pointing indicator on the value of the selected rate (e.g., 15 frames/second), or hovering with the pointing indicator 214 over it. The user may increase the selected rate by moving the pointing indicator to a different location in area 204 (e.g., marked with a value of 22 frames/second). In some embodiments, the user may select a forward/backward direction of playing the stream of images, by moving pointing indicator 214 (e.g., moving pointing device 134 without clicking or providing another indication) from one portion (e.g., sub-portion 210) to another (e.g., sub-portion 206) and/or by pointing a forward or backward mark.

Screen 200 may further include a stream advancement portion 206. Stream advancement portion 206, may include a bar or a scale 205 showing the user the progress of the played stream of images from or relative to where the stream was last stopped. For example, the bar or scale of 205 may indicate to the user if the stream is played forward or backward and approximately what portion (e.g., 1/6) of the stream of images was/is played in from the beginning of the image stream.

In some embodiments, screen 200 may include a horizontal control interface area 208. Horizontal control interface area 208 may be positioned at for example the lower portion of screen 200. The horizontal control interface area may include several control options for controlling the display of the stream of images, for example, start/stop option, frame rate selection, forward/backward selection, etc. The control options in horizontal control area 208 may be selected by a user, for example, by clicking on a pointing device (e.g. controlling a cursor or other on-screen indicator overlaid on an option) or providing another indication. In order to operate the control option in horizontal control area 208, the user may have to shift his vision from the images moving in image stream display area 202 and select a control option by pointing and clicking on the pointing device.

Reference is made to FIG. 2B, showing an example of screen 220 according to some embodiments of the invention. Screen 220 may include at least an image stream display 222 and a speed control area 224. Image stream display area 222 may include the same features and have the same characteristics as image stream display 202 discussed above. Speed control area 224 may include a frame rate control interface 225 including a scale for selecting the frame rate by pointing (e.g., manipulating pointing device 134 such as mouse to control an on-screen pointing indicator 214 or touching the screen) at a location in speed control area 224 (e.g., 8 frames/second). Speed control area 224 may include a single scale with multiple frame rate values for playing the image stream in both the forward and the backward directions. In order to move from forward to backward playing and vice versa, the user may move pointing device 134 such that pointing indicator 214 may point a graphic mark 227 at upper end of speed control area 224. Image stream display area 222 and speed control area 224 may be located on screen 220 such that a user may direct his vision to image stream display area 222 in the screen while moving the pointing indicator 214 in the area of speed control area 224, as discussed above with respect to FIG. 2A. Screen 220 may further include a stream advancement portion (not illustrated) and/or horizontal control area 208 similar to stream advancement portion 206 and horizontal control area 208 discussed above.

Reference is made to FIG. 2C, showing an example of screen 230 according to some embodiments of the invention. Screen 230 may include an image stream display area 232 and a speed control area 234. In some embodiments, screen 230 may include an additional horizontal control area 238. Image stream display area 232 may include a display of two or more image streams to be displayed simultaneously to a user during a single review, for example, a right stream display 240 and a left stream display 242 illustrated in FIG. 2C. The two image streams may be captured simultaneously, e.g., using an imaging capsule with two imaging systems. For example, the right side display may include a stream of images captured in at least one organ in the gastrointestinal tract captured by an imaging system located in one side of an imaging capsule and the left display may be a stream of images captured by an imaging system located at a second, different, side of the imaging capsule. In yet another example, several displays of image streams captured by a plurality of surveillance cameras located at different areas in a bank, a military base, a jail, an embassy or the like, may be displayed simultaneously in image stream display area 232.

Speed control area 234 may include a frame rate control interface 235 for controlling the frame rate in which the images frames are to be displayed in the image stream display area and/or may include a forward/backwards direction control of the movement of the image frames. For example, the user may select the frame rate by moving or pointing (e.g., without clicking on pointing device 134) a pointing indicator 214 (e.g., a cursor) to a location on a frame rate scale 236 indicating a desired frame rate and/or may select a forward/backward display direction by moving or pointing (e.g., without clicking) on a marker 246 at the upper end of speed control area 234. Pointing indicator 214 may be moved for example by moving pointing device 134. The user may control all the displays of the image stream together or may control each display (e.g., displays 242 and 240) separately by clicking on the desired display or may control any section of displays from the plurality of displays simultaneously. In some embodiments, screen 230 may include an additional portion 238 that may include a horizontal control interface at the lower portion of screen 230, similar to the horizontal control interface discussed with respect to FIG. 2A.

Figure 3:
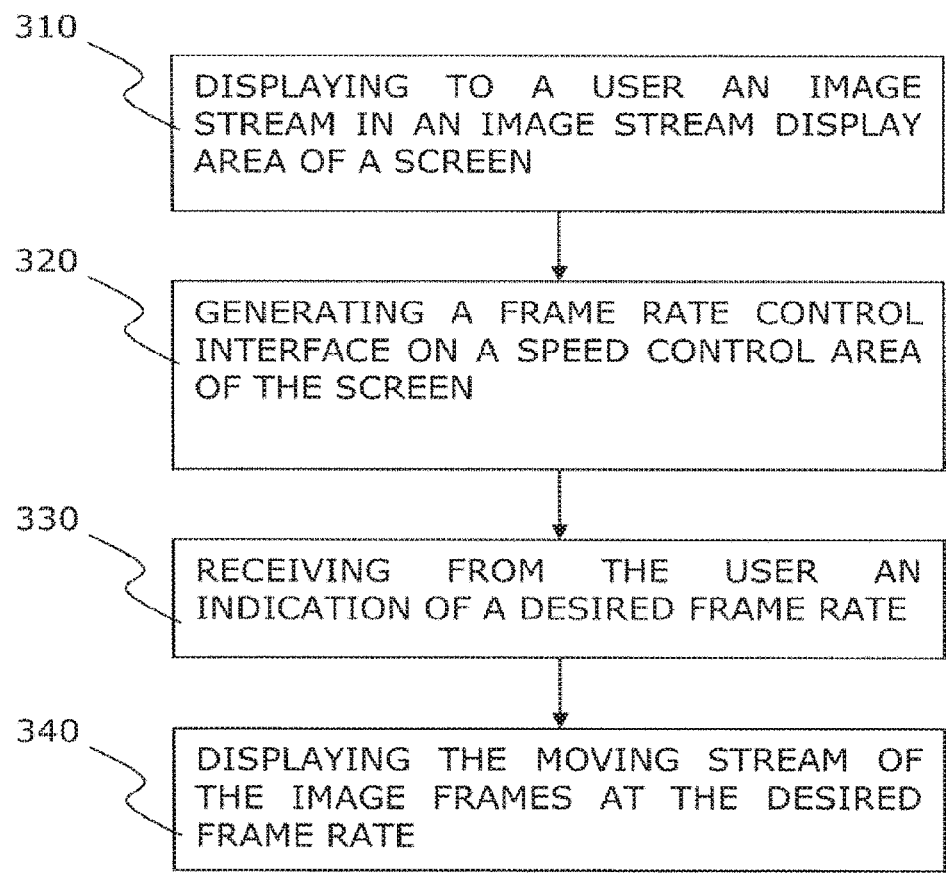
FIG. 3 is a flowchart illustrating a method of controlling the display of an image stream according to embodiments of the invention.

Reference is made to FIG. 3, illustrating a method of controlling a display of an image stream according to embodiments of the invention. The embodiment (as with all embodiments discussed herein) may be executed by a processor (e.g., processor 112 or processor 13) included in a system of displaying and controlling the display of the image stream (e.g., system 100 or workstation 14). Instructions to perform the embodiments (and other embodiments herein) may be stored on a non-volatile memory (e.g., memory 116) to be executed by the processor. In operation 310, an image stream may be displayed to a user in an image stream display area of a screen. The image stream display area may include a single display of moving image streams, for example, the display shown in image stream display areas 202 and 222 of FIGS. 2A and 2B, or may include a plurality of displays, for example, the displays shown in image stream display area 232 of FIG. 2C. The images displayed in the image stream display area may be previously captured by one or more imaging devices (e.g., cameras) and stored in a storing device or a memory accessible to the processor, for example, storing unit(s) 120.

In operation 320, a frame rate control interface may be created, displayed or generated on a speed control area of the screen. The location of the image stream display area in relation to the speed control area may be such that the user may easily direct his vision simultaneously to both portions, substantially without moving his eyes from the image stream display area. Thus, controlling the display of the stream of images is enabled while the user maintains his/her vision focused on the images displayed. In some embodiments, the speed control area may be horizontally adjacent to the image stream display area. In some embodiments, the speed control area may be larger than a predetermined or a calculated threshold; the threshold may be calculated based on the display area of the image stream display. For example, the area of the speed control area may be approximately at least $\frac{1}{7}$ of the area of the image stream display area or between a range of $\frac{1}{10}$-$\frac{1}{3}$.

Generating a frame rate control interface may include generating one or more frame rate scales, having increasing or decreasing frames rates, for example, a scale from 0 to 23 frames/second illustrated in speed control areas 224 and 234 shown in FIGS. 2B and 2C. In yet another example, two frame rate scales may be created, displayed or generated in speed control area 202, shown in FIG. 2A. A first scale 216 for forward playing (e.g., from 0 to 25 frames/second) and a second scale 218 for backward playing (e.g., from 0 to -25 frames/second) may be displayed in speed control area 202.

In operation 330, an indication of a desired frame rate for displaying the stream of the image frames may be received, e.g. from the user. The frame rate may be selected or determined (e.g., by a processor) according to a location of a pointing indicator in the speed control area, such that the user may change the frame rate by moving (e.g., hovering) the pointing indicator inside the speed control area using a pointing device. For example, the processor may receive from a user, via a user interface that includes at least the screen and the pointing device, a location of a pointing indicator (e.g., a cursor). For example, the location of the pointing indicator may be on the frame rate scale at the desired frame rate and the user may change the frame rate by moving the pointing indicator along (e.g., up and down) the frame rate scale using the pointing device (e.g., by moving a mouse or by moving a finger on a touch screen). In some embodiments, the user may select the desired frame rate without clicking (or double clicking/touching) the pointing device, just by moving (e.g., hovering) the pointing indicator.

In operation 340, the image stream may be displayed at the desired frame rate to the user. The movement of the pointing indicator may be done consciously or non-consciously during the display of the moving image streams to the user. A non-consciously movement of the pointing indictor may be the result of an unintentional movement of the pointing device by the user, for example, when the user accidently moves a hand holding a mouse to take a cup of coffee.

Figure 4:
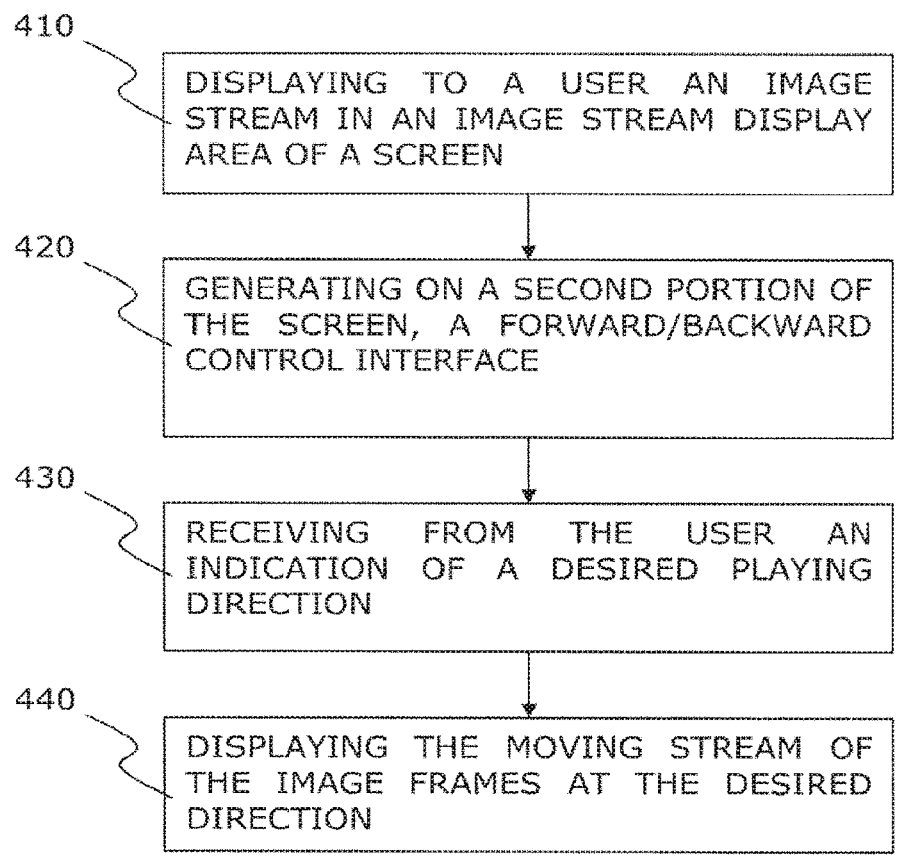
FIG. 4 is a flowchart illustrating a method of controlling the display of an image stream according to embodiments of the invention.

Reference is made to FIG. 4, illustrating a method of controlling a display of an image stream according to embodiments of the invention. In operation 410, an image stream may be displayed to a user in an image stream display area of a screen. Operation 410 may be substantially similar to operation 310, discussed above.

In operation 420, a speed control area may be displayed, created, or generated on the screen including a playback, stop, and forward/backward direction change control interface. The speed control area may be generated such that a user directing his vision to the image stream display area of the screen may be able to control the movement of the pointing indicator, e.g., pointing indicator 214, in the speed control area of the screen. The image stream display area may be horizontally adjacent to the speed control area and/or the speed control area may be larger than a threshold; the threshold may be calculated based on the area of the image stream display. The length of the speed control area may take, for example, up to the whole height of the display area (e.g., speed control area 704). The width of the speed control area may be wide enough such that the user can move pointing indicator, by moving a pointing device, over the speed control area in order to accelerate the viewing speed or reduce the viewing speed, to change direction of the playback, etc., while keeping his/her vision focused on the images displayed in the image stream display area, e.g., without substantially focusing his/her vision on the speed control area. Generating the forward/backward control interface may include generating a graphic mark (e.g., mark 227) in the speed control area and/or generating two graphic marks (e.g., marks 215), optionally at two sub-portions of the speed control area of the screen. For example, the mark or marks may have an arrow shape each located in a different sub-portion, one for forward playing and one for backward playing as shown in FIG. 2A. In yet another example, the marks may include two opposite arrows, as shown in FIG. 2B.

In operation 430, an indication for a desired playing direction may be received from a user. The user may select a desired playing direction by pointing on the graphic marking using a pointing indicator on the forward or backward marking. The user may switch from forward to backward playing by moving the pointing indicator from the forward mark to the backward mark or by moving the pointing indicator from the forward sub-portion to the backward sub-portion. In some embodiments, the selection of the desired playing direction is performed without clicking on the pointing device.

In some embodiments, the user may be alerted when a change in the playing or streaming direction occurs. A graphic mark, for example, change direction alerting mark 219, may appear on the screen each time the streaming or playing direction is changed. In some embodiments, change direction graphic mark 219 may appear as a flickering mark, while in other embodiments change direction graphic mark 219 may appear as a constant mark, or in another form. In yet other embodiments, other displaying methods of change direction graphic mark 219 may be used. The change direction alerting mark 219 may appear at any portion or area of the screen, such that user may keep his/her vision focused on the images displayed. The alert may allow the user to verify that the change in the playing or streaming direction is a desired one, and was not done unintentionally, for example, by unintentional movement of pointing device 134.

In operation 440, the image stream may be displayed at the desired playing direction.

Figure 5:
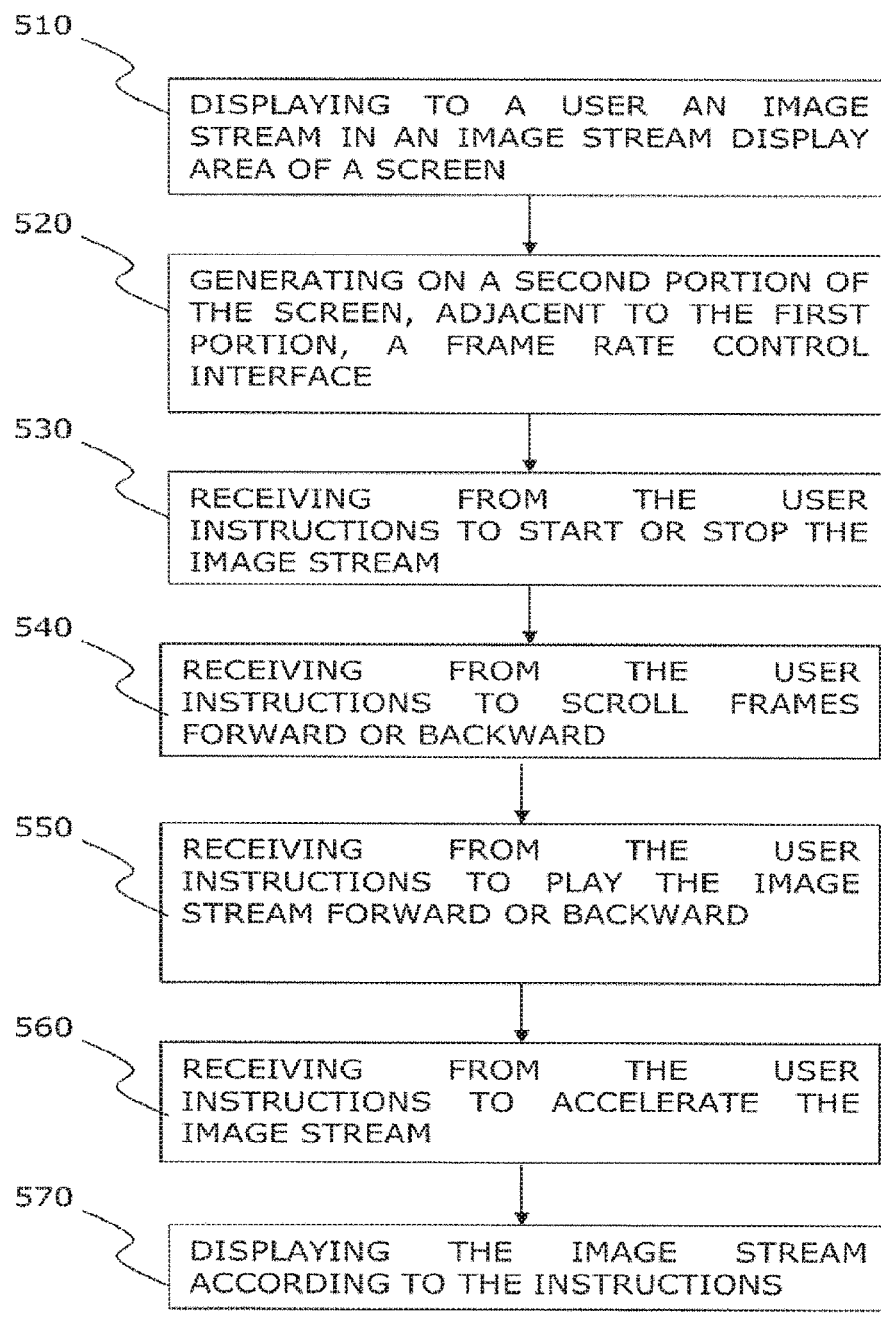
FIG. 5 is a flowchart illustrating a method of controlling the display of an image stream according to embodiments of the invention.

Reference is made to FIG. 5, which illustrates a method of controlling the display of an image stream according to embodiments of the invention. Operations 510 and 520 may be substantially similar to operations 310 and 320, thus will not be discussed again.

In operation 530, instructions to start or stop the playback of the image stream may be received from the user. The user may, for example, click pointing device 134 or provide another indication when pointing indicator 214 is located anywhere in the speed control area of the screen and/or the image stream display of the screen to stop the movement of the stream of images or to start or restart a standing stream (e.g., when a single frame is displayed in the image stream display area of the screen). Stopping the image stream may cause a single, static, frame to be displayed. For example, the system may receive from the user instructions to start or stop the display or the advancement of the stream of the image frames, the instructions being provided or indicated to the processor when the user clicks on or by the user clicking on the pointing device while the pointing indicator is positioned or located in the speed control area.

In operation 540, instructions to scroll or move frames (for example, a single frame each time) forward or backward may be received from the user. These instructions may be provided by the user when the playback of the stream of images is stopped, e.g. following a click on the pointing device or another indication by the user. After stopping the playback, images may be scrolled or moved forward or backward, e.g. one or more frames at a time, by the user using the pointing device. For example, the pointing device may be a mouse, and the instructions to scroll the frames may be received by detecting a rolling movement of a wheel of the mouse. In another example, the instructions to scroll frames may be received by detecting a movement of the pointing indicator inside the speed control area, by moving the pointing device back and forth, up and down, or right and left over the display.

In operation 550, instructions to display or play the stream of image frames backward or forward by pointing at a marker on the speed control area may be received from the user. Operation 550 may include similar features to the ones disclosed above with respect to operations 420 and 430 of the embodiment of the method shown in FIG. 4.

In operation 560, instructions to temporarily accelerate (e.g., increase the speed of display or progress of the stream) of the image frames to a (relatively) high speed may be received from the user. The stream of image frames may be temporarily accelerated by (and an instruction to accelerate may be thus received by the system in response to or as a result of) the user to a maximum frame rate or to a predetermined high frame rate, for example, by clicking (or providing another indication) and holding the pointing device in a clicked position for a period in which the stream of the image frames is to be accelerated to the predetermined high speed. The temporary accelerated rate may be activated during a static or substantially non-changing segment of the image stream, and deactivated (e.g., the user stops pressing on the pointing device's click button) upon identification of an interesting segment or a dynamic segment by the user. For example, the user may click and hold the right or left buttons of a mouse, or touch and hold the finger on a touch screen when a temporarily acceleration of the stream is required. For example, the user may click and hold the right or left buttons of a mouse for 300 milliseconds, thus activating acceleration of the image stream, where the acceleration may occur for as long as the user continues to hold the mouse beyond the initial period. Other periods of time for holding the buttons of a mouse after clicking and thus causing acceleration of the image stream may be used, for example, any time period from 100 milliseconds to 3 seconds. During the acceleration the processor may display to the user the image stream at a rapid frame rate (e.g., 100 frames/second) and/or may display to the user only a portion of the frames, for example, the processor may display one of two consecutive frames, two out of three consecutive frames, 9 out of 10 frames, etc. In some embodiments, upon de-activation of the accelerated rate, the image stream may be played back using the previously-used frame rate, and in another embodiment, the image stream may be automatically stopped or paused until the user selects a new playback frame rate.

In operation 570, the image stream may be displayed according to the received instructions. In some embodiments, only some of operations 530-560 may be performed. For example, only operations 510-540 and 570 may be performed. In some embodiments, operation 330 illustrated in FIG. 3 may be performed in combination with one or more of operations 530-560. The current invention is not limited to any combination of the operations disclosed in any of FIGS. 3-5.

Some aspects of the invention may be related to a system and method for generating an alert to a user who is inspecting an image stream, when the image stream approaches a frame sequence of interest, for example, an alert to the user may be generated by providing a predetermined indication, at a predefined time or a predefined number of frames before the current frame of the displayed image stream reaches or displays the frame sequence of interest. A system for generating the alert may be substantially similar to systems 100 disclosed with respect to FIG. 1A or device 14 disclosed in FIG. 1B. A frame sequence of interest according to embodiments of the invention may include image frames showing an interesting finding (e.g., a pathology candidate) that may require inspection of the stream of image frames at a lower frame rate.

Additionally or alternatively, the frame sequence of interest may include a sequence captured by a moving imaging device, when the imaging device moved at a higher or lower speed than the average speed. The user may decide to inspect the frame sequence of interest at a lower or higher frame rate in order not to lose important information captured in the frame sequence of interest or to move faster at sequences taken at a lower speed. For example, images captured by an imaging device located in an imaging capsule, where there is an indication that the capsule moved at a higher speed than an average (for example, at certain areas in the colon). The indication regarding the capsule's speed may be obtained, for example, from a position detector which may be included in the imaging device, and/or from the image data (e.g. by calculating progress of the capsule based on image registration algorithms). In another example, the image frames may be captured by a camera located on a security car and the frame sequence of interest may be related to a sequence of frames taken during acceleration of the car. In another example, a surveillance camera video may be reviewed. An alert may be provided to the user when an abnormal activity is identified in the stream.

Figure 6:
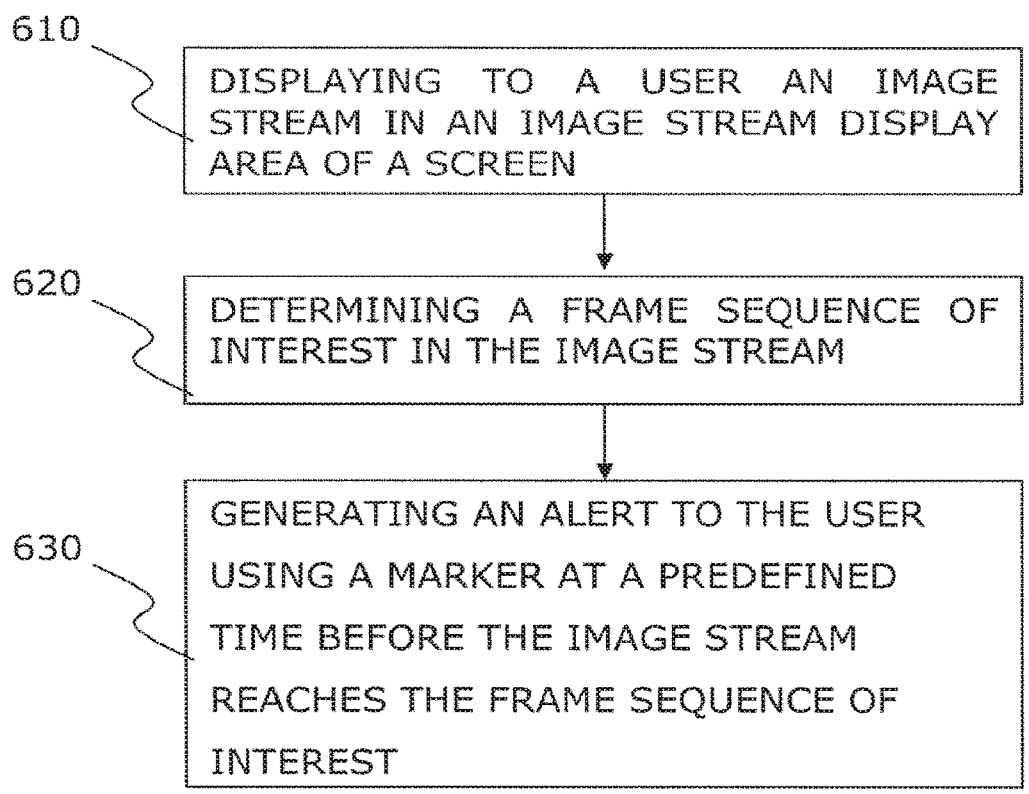
FIG. 6 is a flowchart illustrating a method of generating an alert during screening of the image stream according to embodiments of the invention.

Reference is made to FIG. 6, illustrating a method of generating an alert during review of the image stream according to embodiments of the invention. A memory or a storage-unit associated with the processor (e.g., storage unit 120) may store an image stream including image frames, for example, of at least one organ in a gastrointestinal tract captured by an imaging device included in an imaging capsule or by any other portable and moving imaging device. In operation 610, an image stream may be displayed to a user on a screen. The screen or a portion of the screen may include a single display window of moving image streams, for example, the display shown in image stream display areas 202 and 222 of FIGS. 2A and 2B, or may include a plurality of display windows, for example, the display windows shown in image stream display area 232 of FIG. 2C.

In operation 620, a frame sequence of interest may be determined in the image stream. The frame sequence may include at least two image frames. The frame sequence of interest may include any sequence of images that the user may consider inspecting at a slower rate, or at a higher rate. The sequence may include image(s) of abnormal behavior or interesting findings (e.g., pathology candidate) or may include a sequence of frames that were captured when the imaging device (or an identified object in the images) was moving at a higher speed. Some examples for embodiments of determining a frame sequence of interest are given below.

In operation 630, an alert may be created or generated, or provided, to the user using a marker and/or a sound, the alert generated at a predefined time before the current frame of the displayed image stream reaches or becomes the frame sequence of interest. An alert may be provided, for example, before the time of display of the first frame of the frame sequence. The alert may be generated, for example, 1 second, 2 seconds, 5 seconds or more (or a threshold number of image frames) before the display of the frame sequence of interest. The frame rate which the user uses for displaying the image stream may be used to estimate in which frame/s the alert should be displayed, based on the amount of time which was defined for providing the alert. The amount of time may be configurable by the user, or predetermined and stored in the system. In another example, the number of images in which the alert appears before the identified sequence may be configured by the user. The alert or marker may be a visual indicator (e.g., a graphic sign) that may appear on the screen when the displayed image stream reaches the frame sequence of interest. In some embodiments, the processor may be configured to modify the visual indicator as the image stream approaches the frame sequence of interest, for example, the processor may change the color of the visual indicator, for example, from yellow to orange and then to red as the image stream approaches the frame sequence of interest. In another example, the size and/or brightness/darkness of the indicator may be increased as the image stream approaches the frame sequence of interest. In some embodiments, the processor may be configured to remove the visual indicator at or after the last frame in the frame sequence of interest. The processor may remove the visual indicator immediately (the indicator may appear in one frame and disappear in the next frame) or may gradually disappear over a plurality of frames. In some embodiments, the visual indicator may be an animated object (e.g., an hourglass).

Additionally or alternatively, the marker may be a sound. In some embodiments, the processor may be configured to modify at least one of: the volume or the frequency content of sound emitted to the user, for example, the volume of the sound may be increased and/or the number of sound frequencies may be increased (e.g., a tune may be played) as the image stream approaches the frame sequence of interest. In some embodiments, the processor may be configured to decrease or eliminate the volume and/or the frequency content of the sound at the end of the frame sequence of interest.

Some embodiments may include one or more operations of controlling the display of the image stream as discussed above with respect to FIGS. 3-5. Some embodiments may include controlling the frame rate in which the image stream is to be displayed and/or controlling the forward/backward direction of playing the image stream.

In some embodiments, instruction to automatically decelerate the display rate of the image stream when the image stream approaches a frame sequence of interest may be received from a user. The user may select an automatic deceleration mode prior to playing the image stream or at any stage during the playing of the image stream. After receiving the instruction the processor may decrease the rate at a constant frame rate of any frame sequence of interest until instructed otherwise. At the end of the frame sequence of interest the processor may increase the frame rate to the rate prior to the decrease in display speed. In some embodiments the user may define the accelerated frame rate when selecting the automatic acceleration mode.

In some embodiments, the screen may display an indication of the current frame rate in use. The stream of image frames may include "static" image stream portions in which the images of the image stream remain substantially non-changing and "dynamic" image stream portions in which the images of the image stream change, such that each of said "static" and "dynamic" image stream portions includes multiple image frames. In some embodiments, the "dynamic" image stream portions may be the frame sequence of interest. The processor (e.g., processor 112) may be configured to identify the "static" and "dynamic" image frames. The processor may further be configured to display to the user on the screen (e.g., screens 200, 220 or 230) an indication that the current frame display rate is "static" or "dynamic" frame and the frame rate at which the image stream is displayed. In some embodiments, an indication may be provided only for a "dynamic" portion, or only for a "static" portion. The processor may be configured to automatically adapt the frame rate when the frames displayed are "static" or "dynamic". For example, the processor may increase the frame rate of a "static" image stream portions based on a similarity among multiple images of the "static" image stream portions.

In some embodiments, the processor may display to the user an indication that a "static" or a "dynamic" portion of the image stream is displayed or is about to be displayed, an indication of the current frame rate in use, an indication that the current frame display rate is "basic" or "accelerated", an indication of the relative acceleration of the frame display rate (e.g., twice the "basic" rate, three times the "basic" rate, or the like) or the like. In some embodiments, the processor may present a color indication or an alert, on the screen that the image stream is displayed using an "accelerated" or non-"basic" frame display rate, for example, to alert the user of the current mode of operation. A system and method for automatic control of frame rate according to the "static" or "dynamic" character of the image frames is disclosed in U.S. Patent Publication No. 2008/0051642, entitled "DEVICE, SYSTEM AND METHOD OF DISPLAYING IN-VIVO IMAGES AT VARIABLE RATE", filed Aug. 24, 2006, and assigned to the common assignee of the present application and incorporated herein by reference in its entirety.

Figure 7A:
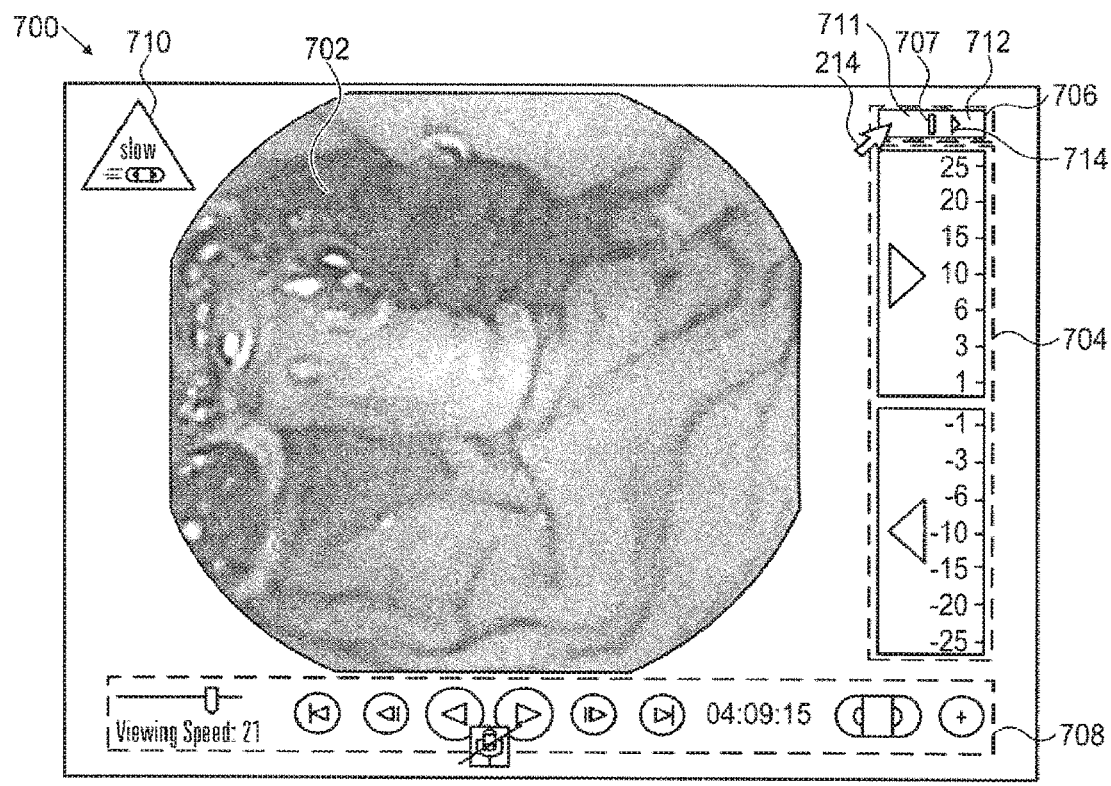
FIG. 7A shows an example of a screen according to some embodiments of the present invention.

An example of screen 700 showing a visual indicator 710 according to some embodiments of the invention is shown in FIG. 7A. Screen 700 may include an image stream display area 702 for displaying an image stream. Image stream display area 702 may display to a user one or more image streams or image steam windows. Additionally screen 700 may include other portions. For example, screen 700 may include a speed control area 704 including a frame rate control interface for controlling the frame rate in which the images frames are to be displayed in image stream display area 702 and/or a forward/backwards direction control of the movement of the image frames according to some embodiments of the present invention.

Screen 700 may include a stream advancement portion 706 including a bar or a scale showing the user the progression of the played image stream, in relation to the frame where the stream was last stopped or paused. The stream advancement portion 706 may display to a user the distance (measured, for example, in frames or time) between the current frame displayed in the image steam stream portion, and the last stop or pause of the image stream. The stream advancement portion 706 may allow a user to easily return to the point or frame of the previous stop, for example, by clicking on the middle line 707 of stream advancement portion 706. In another example, stream advancement portion 706 may enable "rewinding" the movie (or repositioning the start of playback) a predefined amount of frames backwards from the current frame, e.g., by clicking a pointing device 214 on the left side 711 of stream advancement portion 706. Similarly, the stream may be advanced forward a predetermined amount of frames or a predetermined amount of time by clicking on the right side 712 of stream advancement portion 706. The amount of image frames that may be skipped from the current frame when clicking or pointing at right side 712 may be predetermined in the system, e.g., 50 frames, and/or may be configurable by a user. Similarly, when clicking or pointing at left side 711, the amount of frames which the current frames of the image stream is returned may be predetermined, e.g., 50 frames, and/or configurable by a user.

When a user scrolls through images using the stream advancement portion 706, e.g., after stopping a moving display of the image steam, an indicator 714 may indicate in which direction the user is scrolling, e.g., relative to the image at which the moving display was stopped. For example, indicator 714 may have the shape of an arrow. When indicator 714 is pointing to the right it may indicate that the user's scrolling is causing the image stream to advance forward, and when indicator 714 is pointing to the left it may indicate that the user's scrolling is causing the image stream to return backwards. Other directions, and meanings of directions, may be used. The stream advancement portion 706 may enable the indicator to move a predetermined (or configurable) amount of frames to the left or to the right. If the user scrolls further after the predetermined amount of images, another indication may appear. For example, left side 711 or right side 712 may be displayed using a different color. Other indications may be used. When a user changes the scrolling direction, and continues scrolling past the image at which the moving display was last stopped, an indication may be displayed to alert the user that the direction of scrolling has changed, and that the movie is being displayed in a different direction than previously. Indicator 714 may be changed according to the selected display method, e.g., when the user selects a display mode which shows only suspected bleeding images, the indicator 714 may be displayed in a red (or other) color. Similarly, if the user selects a display mode in which only a portion of the captured images are displayed according to certain selection criteria, the indicator 714 may change accordingly to indicate the selected display method.

In some embodiments, once display of image streams in image stream display area 702 continues, the last stop or pause of the image stream is cleared and a new stop or pause of the image stream is then available to be activated by the user.

Figure 7B:
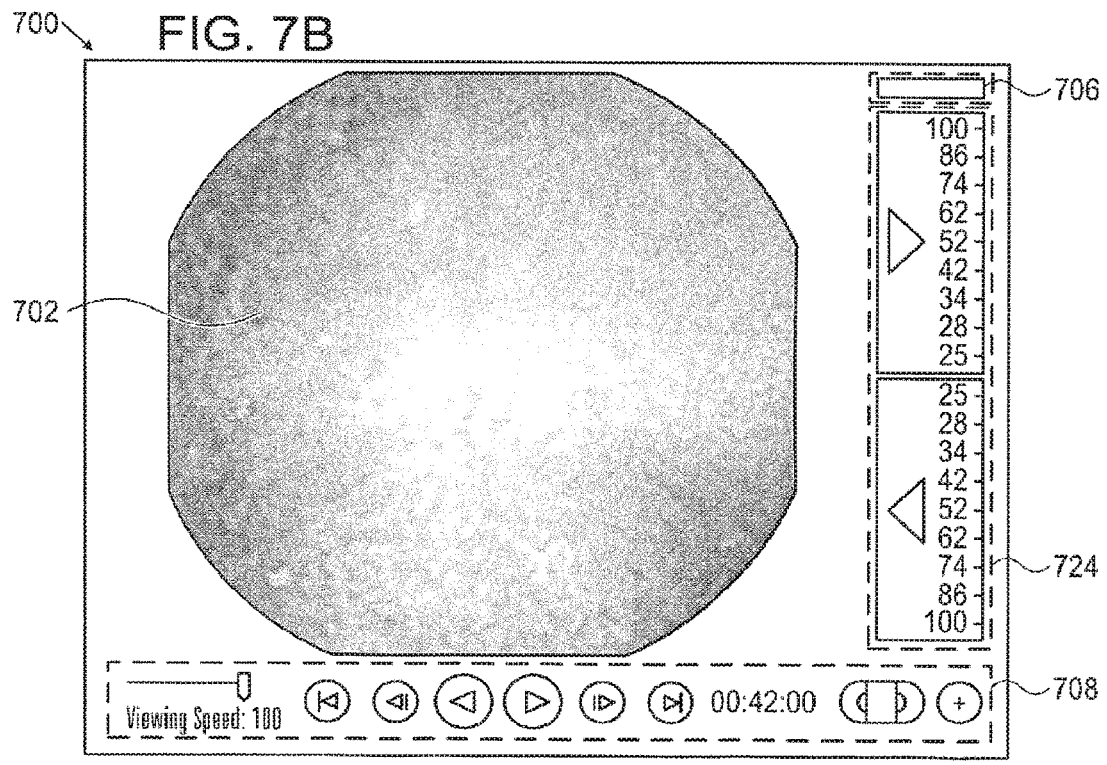
FIG. 7B shows an example of a screen during an accelerated mode according to some embodiments of the present invention.

In a 'regular' or 'normal' display mode, the frame rate may be selected by the user using a scale of, for example, 0-25 frames per second, for a forward playing direction and a backward playing direction, e.g., as currently appears in area 704. In an 'accelerated' display mode, which may be activated, for example, by a user when clicking and holding a button on the pointing device, the frame rate scale may change to support selection of an accelerated frame display rate, e.g., the user may select a frame rate of, for example, 25-100 frames per second, as shown, for example, in area 724 in FIG. 7B. During the accelerated mode the scale in the speed control area changes, for example, from a scale of 0-25 frames per second in area 704 to a scale of 25-100 frames per second in area 724. Once the user stops holding the button clicked, the display may return to the 'normal' (un-accelerated) display mode (e.g., speed control area 704).

The frame rate selection scale in area 704 may also change when a different window display mode is selected, e.g., a dual window showing two images of the image stream (or of two streams) simultaneously (e.g., as shown in FIG. 2C), a quad window showing four image stream windows simultaneously, etc. In some embodiments, a color indication may be applied to the frame rate selection area when the accelerated mode is activated, to alert the user to the special mode of display. Other alerts may be issued or displayed to indicate a certain display mode to the user.

Screen 700 may further include playback control portion 708 including a horizontal control interface at the lower section of screen 700. The horizontal control interface may include several control options for controlling the display of the image stream according to some embodiments of the invention.

Figure 8:
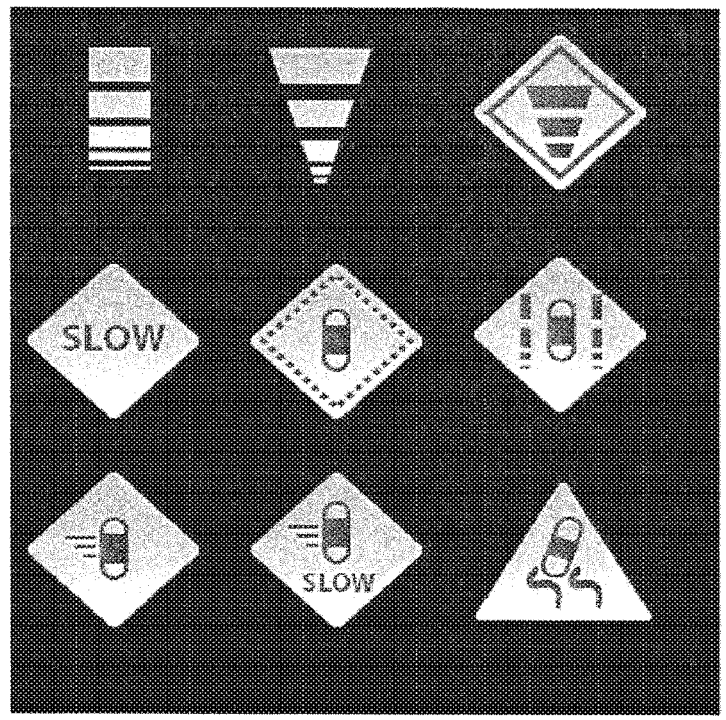
FIG. 8 shows examples of visual indicators according to some embodiments of the present invention.

Visual indicator 710 may be, for example, any graphical sign that may alert a user. Some examples for graphical signs which may be used as visual indicators are shown in FIG. 8. In yet another example, the visual indicator may be an animated object (e.g., a flickering flash light) that may move or change as the image stream approaches the frame sequence of interest and/or during the inspection (review) of the frame sequence of interest.

Figure 9:
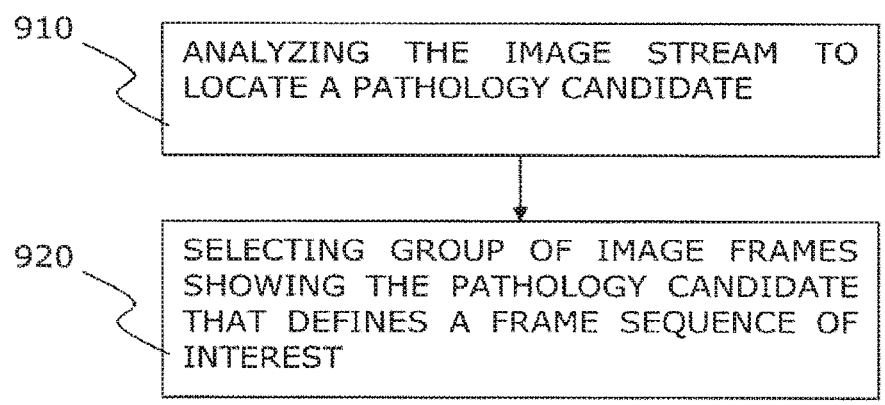
FIG. 9 is a flowchart illustrating a method of determining a frame sequence of interest in an image frame according to some embodiments of the present invention.

Reference is made to FIG. 9, which illustrates a method of determining a frame sequence of interest in an image stream according to some embodiments of the present invention. In operation 910 the image stream may be analyzed to locate a pathology candidate. The image stream may include images of pathology candidates, for example, ulcers, polyps, tumors, suspected bleeding or red areas, etc. A pathology candidate may be detected by a pathology detector. The processor (e.g., processor 112) may analyze the images included in the image stream to locate pathology candidates. There are several methods for analyzing images captured, for example, from an organ in the gastrointestinal tract. For example, image data or image properties related to a manifestation of a pathology candidate in an image (e.g., properties relating to a pathology candidate's shape, color, density, etc.) may be stored in a memory or a storage unit associated with the processor. The processor may compare the image data with an object located in images included in the image stream, and select one or more image frames each showing an object having a similarity to the stored image data.

An example of a method of identifying (by a processor) pathology candidates may include identifying elliptical forms in the stored image frames. The method may further include extracting data related to each elliptical form identified, for example, the color, the size, the aspect ratio or the like. The processor may compare the extracted data with a data stored in a memory or a storage unit associated with the processor. For example, the memory or storage unit may include lookup table(s) including lists of combinations of sizes, colors and aspect ratios that may be related to typical pathology candidates, for example, polyps, and may further compare the data stored in the lookup table with the extracted data. The method may further include determining if a pathology candidate is shown in a frame based on the comparison. A method and system for detecting and identifying pathology candidates is disclosed in U.S. Pat. No. 8,423,123, entitled "SYSTEM AND METHOD FOR IN-VIVO FEATURE DETECTION" filed Sep. 30, 2005, assigned to the common assignee of the present application and incorporated herein by reference in its entirety. Another example of a method for detection of abnormalities in vivo is disclosed in U.S. Patent Publication No. 2002/0177779 entitled "Method and system for detecting colorimetric abnormalities in vivo" filed Mar. 14, 2002, assigned to the common assignee of the present application and incorporated herein by reference in its entirety. Other methods may be used. In some embodiments, other frames of interest may be detected, for example, anatomical landmarks or transition points in the in vivo lumen such as the duodenum, the pylorus, the cecum, the Z-line, etc. An example of a method for detecting a transition point in an image stream is disclosed in U.S. Pat. No. 7,684,599, entitled "System and method to detect a transition in an image stream", assigned to the common assignee of the present application and incorporated herein by reference in its entirety.

In operation 920, at least one group of image frames showing the pathology candidate may be selected, such that the group defines a frame sequence of interest. One or more consecutive image frames identified as showing the same pathology candidates may be selected as the frame sequence of interest.

In some embodiments, the frame sequence of interest may include image frames that were captured when the imaging device (e.g., an imaging device included in an imaging capsule) moved at a higher speed. In some embodiments, it is possible to determine a parameter indicative of a speed of the movement of the capsule in the gastrointestinal tract (e.g., in at least one organ included in the gastrointestinal tract). For example, the parameter may be related to substantially large changes between consecutive frames. A large difference between two consecutive frames may indicate that the capsule moved rapidly from the position where a first image was captured to another position (e.g., at a different section of the organ) where a second image was captured. The processor (e.g., processor 112) may be configured to analyze the image frames and to identify differences between two consecutive images. The calculated difference or the degree of similarity may be scored or assigned a parameter that is indicative of the capsule's movement, e.g., a high score may be assigned to an image which is very different from the previous image captured by the in vivo device, and a low score is assigned to an image which is substantially similar to the previously captured image in the image stream. A higher score indicates a faster movement of the capsule. Other methods may be used to determine when the imaging device moved at a higher speed, for example, a positioning unit which may be included in the imaging device, such as an accelerometer, may provide indication of the capsule's position in time, and the speed may be derived from the position/time data.

In another example, an identified object in an image may move, while the imaging device remains substantially immobile, e.g., a surveillance camera. Thus, the frame sequence of interest may include image frames that were captured when the object of interest moved at a higher speed. A measure of difference (or similarity) between consecutive images of the image stream may be used to determine the object's speed, or to determine whether to alert the user regarding a fast motion frame sequence.

Figure 10:
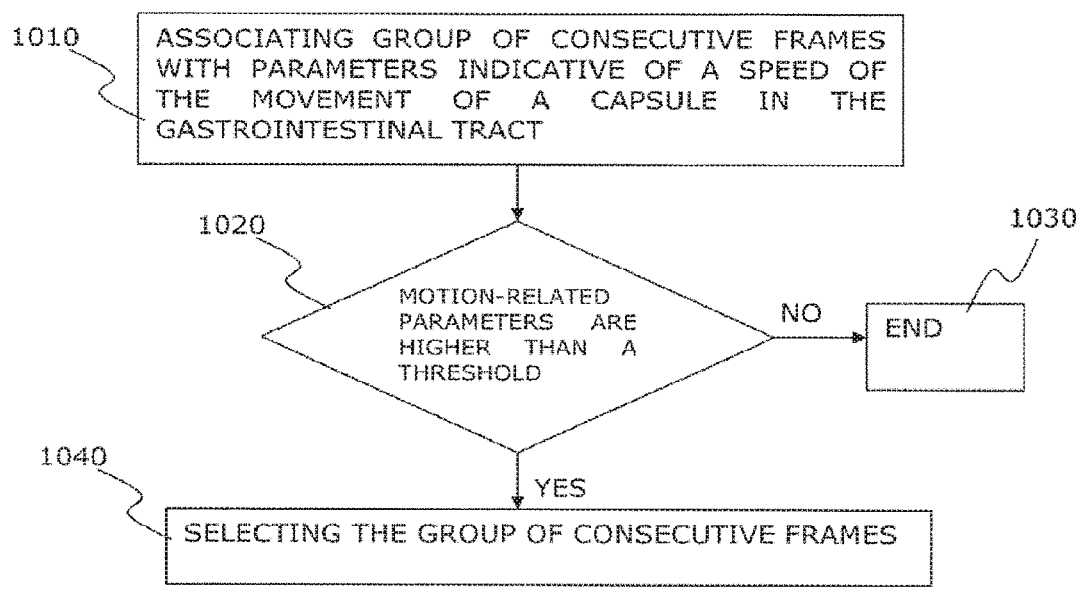
FIG. 10 is a flowchart illustrating a method of determining a frame sequence of interest in an image frame according to some embodiments of the present invention.

Reference is made to FIG. 10, illustrating a method of determining a frame sequence of interest in the image frame according to some embodiments of the present invention. In operation 1010, consecutive frames may be associated with motion-related parameters indicative of a speed of the movement of a capsule in the gastrointestinal tract, or a speed of an object tracked by an immobile imaging device. The parameters may be determined based on a change between the two consecutive image frames, or based on a localization unit which may be included in the capsule. Examples of changes between consecutive image frames may include: a size of an object in the image frame, a color or texture of the object or a color or texture of the background.

Figure 12:
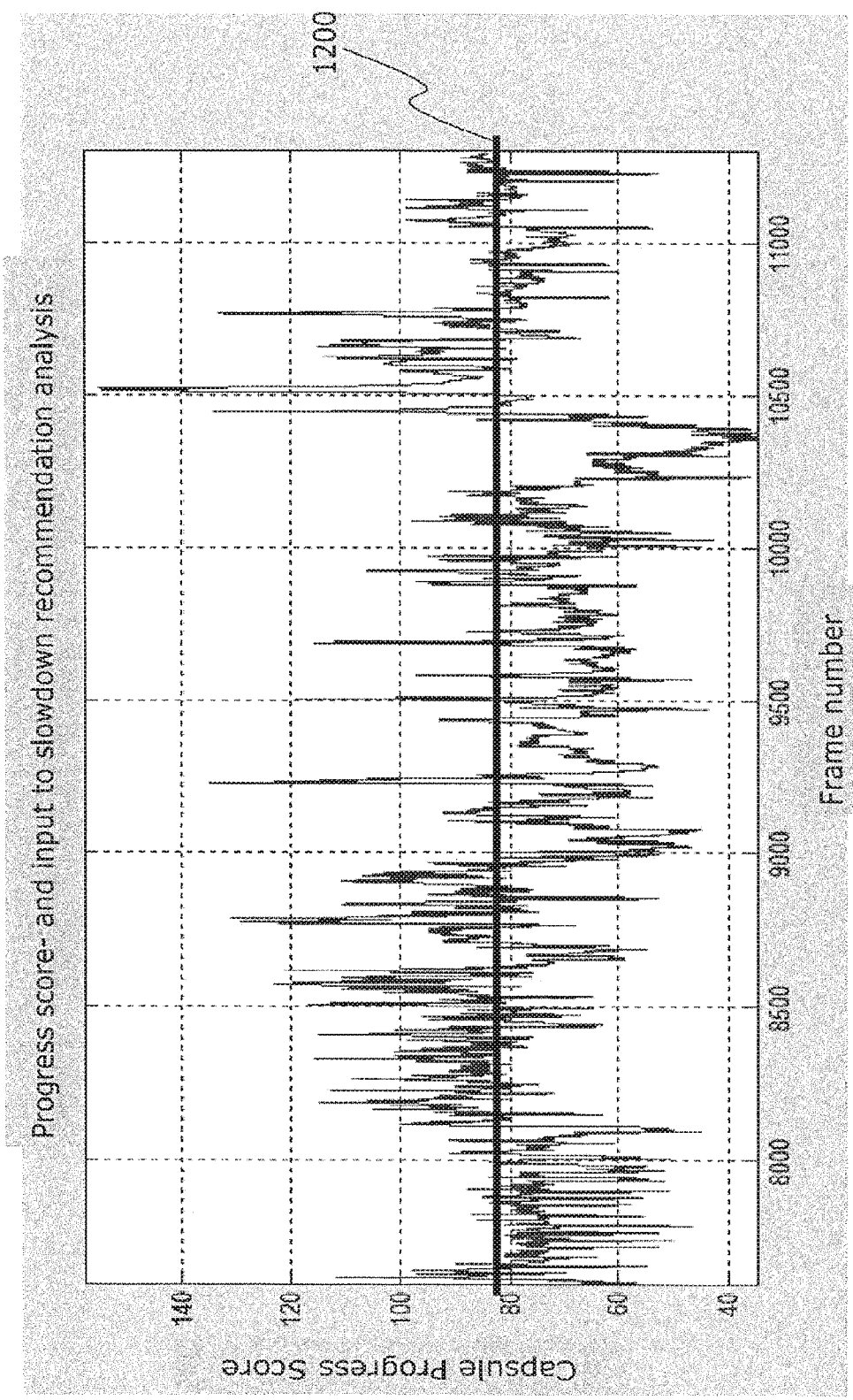
FIG. 12 is a graph presenting a parameter indicative of a speed or the movement of a capsule in the gastrointestinal tract calculated for each frame according to some embodiments of the invention.

In operation 1020, a decision may be made if the motion-related parameters are higher than a threshold value. For example, a value indicated by a bold line 1200 illustrated in FIG. 12 may be set as a threshold value. FIG. 12 depicts a graph in which the y-axis is the motion-related parameter and the x-axis is the sequential frame identification numbers, which are assigned to each image captured; the graph is discussed herein below with respect to FIG. 12. If the motion-related parameters are lower than the threshold value, the image frames may not be selected as a frame sequence of interest and the process may end, in operation 1030. If the parameters are higher than the threshold value, in operation 1040, at least one group of consecutive frames associated with motion-related parameters larger than the threshold value may be selected. The processor may store the frame selection for a further use in methods of generating an alert during review of an image stream according to embodiments of the invention.

Figure 11:
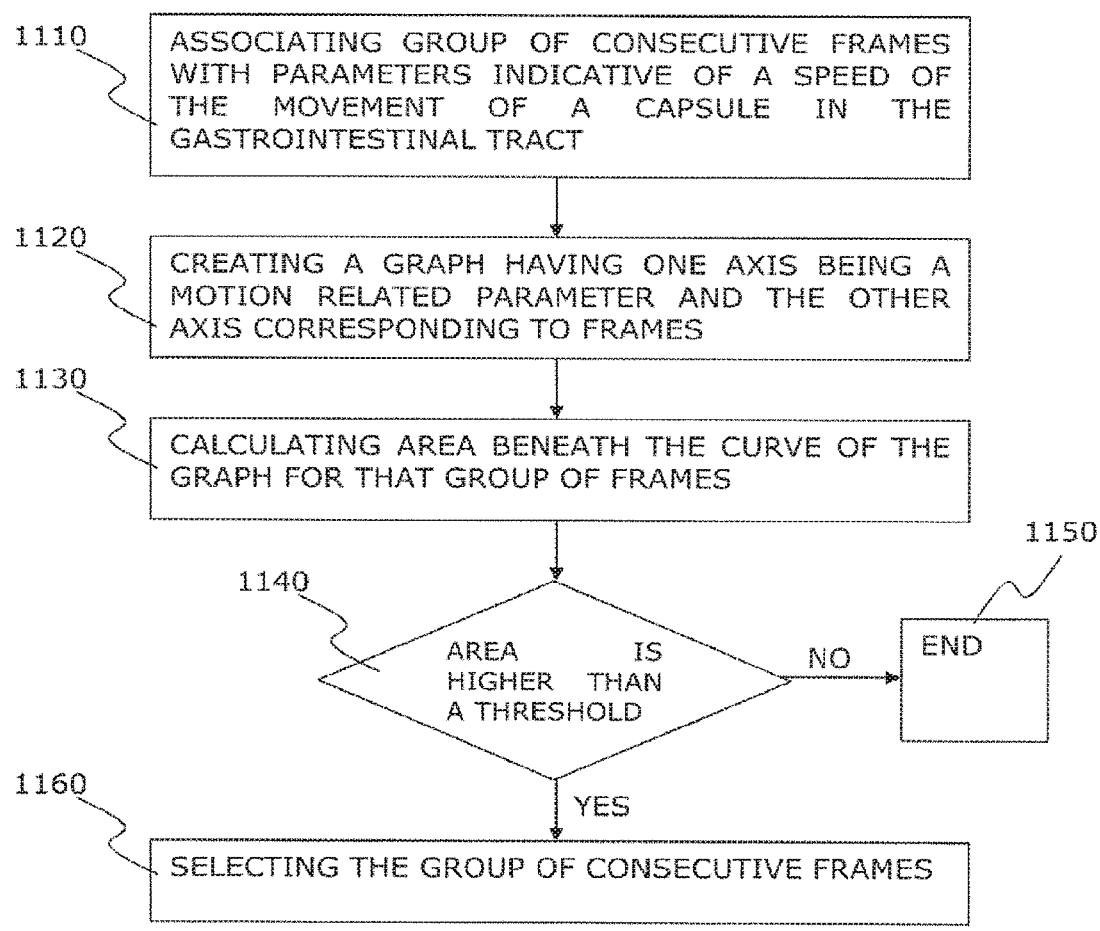
FIG. 11 is a flowchart illustrating a method of determining a frame sequence of interest in an image frame according to some embodiments of the present invention.

Reference is made to FIG. 11, which illustrates a method of determining a frame sequence of interest in the image frame according to some embodiments of the present invention. In operation 1110, consecutive frames may be associated with motion-related parameters (e.g., scores) indicative of a speed of the movement of a capsule in the gastrointestinal tract. The motion-related parameters may be determined based on a change between two consecutive image frames. The change may be in: a size of an object in the image frame, a color of the object or a color or texture of the background.

In operation 1120, a graph may be created having one axis being an indication or a score correlating to the amount of motion detected in the image data or in position data of the in vivo device and the other axis corresponding to frame sequence numbers. An example of a graph is shown in FIG. 12. The graph includes a vertical axis being the motion-related parameter (e.g., a score) indicative of the speed of the movement of the capsule in the gastrointestinal tract and a horizontal axis corresponding to the frames. A threshold line 1200 divides consecutive groups of frames into two types. The first type has motion-related parameters associate with the frames in the group above the threshold line and the second type has motion-related parameters associated with the frames in the group below the threshold line. A group of image frames associated with motion-related parameters higher than the threshold may be captured when the imaging capsule moved at a speed higher than image frames associated with motion-related parameters lower than the threshold. Some groups include larger number of consecutive frames than others.

In operation 1130, an area beneath the curve of the graph may be calculated for a group of consecutive frames, for example, for all the groups having motion-related parameters associated with the frames above the threshold line. For each group, the area beneath the curve may be calculated, using any known method. A second threshold value may be determined related to the area beneath the curve. A calculated area higher than the threshold may be indicative that the group of consecutive images frames was captured at a higher speed for a relatively longer period of time, and not due to a momentary increase in the speed of the capsule. The calculated area for each group may be compared to the second threshold value in operation 1140. If the area calculated is lower than the second threshold value, it may be determined that the frames were captured during a momentary increase in the capsule's speed, and may not be regarded as a frame sequence of interest, in operation 1150.

If the area calculated is higher than the second threshold value, in operation 1160, a group of image frames may be selected to be regarded as a frame sequence of interest. If two areas are detected close to each other (e.g., closer than a predetermined threshold), the areas may be combined into a single frame sequence of interest. This may improve the user's experience, since it may be confusing to receive repeated indications of interesting areas which appear very shortly one after the other during the image stream review.

Various embodiments have been presented. Each of these embodiments may of course include features from other embodiments presented, various embodiments presented are combinable with the other embodiments disclosed herein, and embodiments not specifically described may include various features described herein.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

What is claimed is:

1. A system for controlling display of an image stream, comprising:
   a storage configured to store the image stream, the image stream comprising image frames of at least a portion of a gastrointestinal tract captured by an imaging device in an imaging capsule;
   a processor; and
   a memory storing instructions which, when executed by the processor, cause the system to:
      display on a screen at least a portion of the image stream, the at least the portion of the image stream displayed in a center portion of the screen;
      display on the screen a stream advancement bar configured to show a display progression of the image stream, the stream advancement bar displayed on the screen separately from the center portion;
      display on the screen a frame rate control interface comprising:
         a first scale configured to set an advance forward display frame rate, and
         a second scale, separate from the first scale, configured to set a return backward display frame rate,
         wherein the frame rate control interface is configured to permit the advance forward display frame rate and the return backward display frame rate to be separately set, and
         wherein the frame rate control interface is displayed on the screen separately from the center portion and from the stream advancement bar;
      display on the screen a playback control interface comprising a start selection, a stop selection, a forward selection, a backward selection, and a viewing speed selection, wherein the playback control interface is displayed on the screen separately from the center portion, from the stream advancement bar, and from the frame rate control interface;
      control display of the image stream based on user engagement of one or more of the stream advancement bar, the frame rate control interface, and the playback control interface;
      in response to a user engagement of a first side of the stream advancement bar, display the image stream in a backward direction;
      in response to a user engagement of a second side of the stream advancement bar, display the image stream in a forward direction; and
      display in the stream advancement bar an indication that the image stream is displaying in the backward direction or the forward direction.

2. The system of claim 1, wherein in controlling display of the image stream, the instructions, when executed by the processor, cause the system to, for user engagement of the frame rate control interface:
   in response to a user engagement of a portion of the first scale, set the advance forward display frame rate in accordance with the user engagement and display the image stream in a forward direction in accordance with the advance forward display frame rate; and
   in response to a user engagement of a portion of the second scale, set the return backward display frame rate in accordance with the user engagement and display the image stream in a backward direction in accordance with the return backward display frame rate.

3. The system of claim 2, wherein in controlling display of the image stream, the instructions, when executed by the processor, cause the system to, for user engagement of the playback control interface, display the image stream in accordance with the user engagement of one of the start selection, the stop selection, the forward selection, or the backward selection, wherein a speed of displaying the image stream is based on a setting of the viewing speed selection.

4. The system of claim 1, wherein the instructions, when executed by the processor, further cause the system to:

display on the screen a direction alerting mark, wherein the direction alerting mark is displayed on the screen separately from the center portion, from the stream advancement bar, from the frame rate control interface, and from the playback control interface.

5. The system of claim 1, wherein the instructions, when executed by the processor, further cause the system to:

determine a distance between a first frame in the image stream and a second frame in the image stream, wherein the first frame is a previously paused frame and the second frame is a frame currently displayed on the screen; and display the distance in the stream advancement bar, wherein the distance is measured in one of a number of frames or an amount of time.

6. The system of claim 1, wherein the instructions, when executed by the processor, further cause the system to:

display on the screen a visual indicator comprising at least one of a graphical mark or an animated object, wherein the visual indicator is displayed on the screen separately from the center portion, from the stream advancement bar, from the frame rate control interface, and from the playback control interface; and modify the visual indicator in response to an event, wherein modifying the visual indicator comprises changing at least one of a color, a size, or a brightness of the visual indicator.

7. A method for controlling display of an image stream, the method comprising:

displaying on a screen at least a portion of an image stream, the at least the portion of the image stream displayed in a center portion of the screen;

displaying on the screen a stream advancement bar configured to show a display progression of the image stream, the stream advancement bar displayed on the screen separately from the center portion;

displaying on the screen a frame rate control interface comprising:

a first scale configured to set an advance forward display frame rate, and a second scale, separate from the first scale, configured to set a return backward display frame rate, wherein the frame rate control interface is configured to permit the advance forward display frame rate and the return backward display frame rate to be separately set, and wherein the frame rate control interface is displayed on the screen separately from the center portion and from the stream advancement bar;

displaying on the screen a playback control interface comprising a start selection, a stop selection, a forward selection, a backward selection, and a viewing speed selection, wherein the playback control interface is displayed on the screen separately from the center portion, from the stream advancement bar, and from the frame rate control interface;

controlling display of the image stream based on user engagement of one or more of the stream advancement bar, the frame rate control interface, and the playback control interface, in response to a user engagement of a first side of the stream advancement bar, displaying the image stream in a backward direction;

in response to a user engagement of a second side of the stream advancement bar, displaying the image stream in a forward direction; and displaying in the stream advancement bar an indication that the image stream is displaying in the backward direction or the forward direction.

8. The method of claim 7, wherein controlling display of the image stream comprises, for user engagement of the frame rate control interface:

in response to a user engagement of a portion of the first scale, setting the advance forward display frame rate in accordance with the user engagement and displaying the image stream in a forward direction in accordance with the advance forward display frame rate; and in response to a user engagement of a portion of the second scale, setting the return backward display frame rate in accordance with the user engagement and displaying the image stream in a backward direction in accordance with the return backward display frame rate.

9. The method of claim 8, wherein controlling display of the image stream comprises, for user engagement of the playback control interface, displaying the image stream in accordance with the user engagement of one of the start selection, the stop selection, the forward selection, or the backward selection, wherein a speed of displaying the image stream is based on a setting of the viewing speed selection.

10. The method of claim 7, further comprising:

displaying on the screen a direction alerting mark, wherein the direction alerting mark is displayed on the screen separately from the center portion, from the stream advancement bar, from the frame rate control interface, and from the playback control interface.

11. The method of claim 7, further comprising:

determining a distance between a first frame in the image stream and a second frame in the image stream, wherein the first frame is a previously paused frame and the second frame is a frame currently displayed on the screen; and displaying the distance in the stream advancement bar, wherein the distance is measured in one of a number of frames or an amount of time.

12. The method of claim 7, further comprising:

displaying on the screen a visual indicator comprising at least one of a graphical mark or an animated object, wherein the visual indicator is displayed on the screen separately from the center portion, from the stream advancement bar, from the frame rate control interface, and from the playback control interface; and modifying the visual indicator in response to an event, wherein modifying the visual indicator comprises changing at least one of a color, a size, or a brightness of the visual indicator.

13. A non-transitory processor-readable storage medium storing instructions which, when executed by a processor, cause performance of a method for controlling a display of an image stream, the method comprising:

displaying on a screen at least a portion of the image stream, the at least the portion of the image stream displayed in a center portion of the screen;

displaying on the screen a stream advancement bar configured to show a display progression of the image stream, the stream advancement bar displayed on the screen separately from the center portion;

displaying on the screen a frame rate control interface comprising:
- a first scale configured to set an advance forward display frame rate, and
- a second scale, separate from the first scale, configured to set a return backward display frame rate,
- wherein the frame rate control interface is configured to permit the advance forward display frame rate and the return backward display frame rate to be separately set, and
- wherein the frame rate control interface is displayed on the screen separately from the center portion and from the stream advancement bar;

displaying on the screen a playback control interface comprising a start selection, a stop selection, a forward selection, a backward selection, and a viewing speed selection, wherein the playback control interface is displayed on the screen separately from the center portion, from the stream advancement bar, and from the frame rate control interface;

controlling display of the image stream based on user engagement of one or more of the stream advancement bar, the frame rate control interface, and the playback control interface;

in response to a user engagement of a first side of the stream advancement bar, display the image stream in a backward direction;

in response to a user engagement of a second side of the stream advancement bar, display the image stream in a forward direction; and display in the stream advancement bar an indication that the image stream is displaying in the backward direction or the forward direction.

14. The non-transitory processor-readable storage medium of claim 13, wherein controlling display of the image stream comprises, for user engagement of the frame rate control interface:
- in response to a user engagement of a portion of the first scale, setting the advance forward display frame rate in accordance with the user engagement and displaying the image stream in a forward direction in accordance with the advance forward display frame rate; and
- in response to a user engagement of a portion of the second scale, setting the return backward display frame rate in accordance with the user engagement and displaying the image stream in a backward direction in accordance with the return backward display frame rate.

15. The non-transitory processor-readable storage medium of claim 14, wherein controlling display of the image stream comprises, for user engagement of the playback control interface, displaying the image stream in accordance with the user engagement of one of the start selection, the stop selection, the forward selection, or the backward selection,
- wherein a speed of displaying the image stream is based on a setting of the viewing speed selection.

16. The non-transitory processor-readable storage medium of claim 13, the method further comprising:
- displaying on the screen a direction alerting mark, wherein the direction alerting mark is displayed on the screen separately from the center portion, from the stream advancement bar, from the frame rate control interface, and from the playback control interface.

17. The non-transitory processor-readable storage medium of claim 13, the method further comprising:
- determining a distance between a first frame in the image stream and a second frame in the image stream, wherein the first frame is a previously paused frame and the second frame is a frame currently displayed on the screen; and
- displaying the distance in the stream advancement bar, wherein the distance is measured in one of a number of frames or an amount of time.

18. The non-transitory processor-readable storage medium of claim 13, the method further comprising:
- displaying on the screen a visual indicator comprising at least one of a graphical mark or an animated object, wherein the visual indicator is displayed on the screen separately from the center portion, from the stream advancement bar, from the frame rate control interface, and from the playback control interface; and
- modifying the visual indicator in response to an event, wherein modifying the visual indicator comprises changing at least one of a color, a size, or a brightness of the visual indicator.

* * * * *